US007553926B2

(12) United States Patent
Savarino et al.

(10) Patent No.: US 7,553,926 B2
(45) Date of Patent: Jun. 30, 2009

(54) COMPOSITIONS CONTAINING ANTI-HIV PEPTIDES AND METHODS FOR USE

(76) Inventors: Andrea Savarino, Via Rocciamelone 10, 1-10048, Vinovo (TO) (IT); Umberto Dianzani, Corso Ferrucci 56, 1-10138, Torino (IT)

( * ) Notice: Subject to any disclaimer, the term of this patent is extended or adjusted under 35 U.S.C. 154(b) by 900 days.

(21) Appl. No.: 10/421,664

(22) Filed: Apr. 23, 2003

(65) Prior Publication Data

US 2004/0116653 A1 Jun. 17, 2004

Related U.S. Application Data

(60) Provisional application No. 60/441,346, filed on Jan. 20, 2003, provisional application No. 60/428,734, filed on Nov. 23, 2002, provisional application No. 60/401,587, filed on Aug. 6, 2002, provisional application No. 60/375,105, filed on Apr. 23, 2002.

(51) Int. Cl.
*A61K 38/00* (2006.01)
(52) U.S. Cl. ........................ 530/300; 530/324; 530/325; 530/326; 530/327
(58) Field of Classification Search .............. 424/188.1, 424/208.1
See application file for complete search history.

(56) References Cited

U.S. PATENT DOCUMENTS

| 5,622,933 | A | 4/1997 | Sabatier et al. | ................ 514/16 |
| 5,800,822 | A | 9/1998 | Sia et al. | .................. 424/208.1 |
| 6,114,143 | A | 9/2000 | Eda et al. | .................... 435/69.3 |
| 6,193,981 | B1 | 2/2001 | Goldstein | ................ 424/208.1 |
| 6,258,932 | B1 | 7/2001 | Vahlne | ........................ 530/331 |

FOREIGN PATENT DOCUMENTS

| WO | WO 93/04693 | 3/1993 |
| WO | WO 94/17184 | 8/1994 |

OTHER PUBLICATIONS

Savarino, A., et al., 1999, Effects of the human CD38 glycoprotein on the early stages of the HIV-1 replication cycle, The FASEB J. 13:2265-2276.*
Munshi, C., et al., 1999, "Characterization of the active site of ADP-ribosyl cyclase", J. Biol. Chem. 274(43):30770-7 (abstract provided).*
Munshi, C., et al., 2000, "Identification of the enzymatic active site of CD38 by site-directed mutagenesis", J. Biol. Chem. 275(28): 21566-71 (abstract provided).*
Tohgo, A., et al., 1997, "Lysine 129 of CD38 (ADP-ribosyl cyclase/ cyclic ADP-ribose hydrolase) participates in the binding of ATP to inhibit the cyclic ADP-ribose hydrolase", J. Biol. Chem. 272(7):3879-82 (abstract provided).*
Hoshino, S., et al., 1997, "Mapping of the catalytic and epitopic sites of human CD38/NAD+ glycohydrolase to a functional domain in the carboxyl terminus", J. Immunol. 158(2):741-7 (abstract provided).*

Savarino, et al., Human CD38 interferes with HIV-1 fusion through a sequence homologous to the V3 loop of the viral envelope glycoprotein gp120[1]. The FASEB Journal, 2003, vol. 17, p. 461-463.
Fantini, et al., Multi-branched peptides based on the HIV-1 V3 loop consensus motif inhibit HIV-1 and HIV-2 infection in CD4+ and CD4− cells. C. R. Acad. Sci. Paris, Sciences de la vie/Life sciences, 1993, vol. 316, p. 1381-7.
Yahi, et al., Multibranched V3 Peptides Inhibit Human Immunodeficiency Virus Infection in Human Lymphocytes and Macrophages. Journal of Virology, 1994, p. 5714-5720.
Fantini Jacques et al., Multi-Branched Peptides Based on the HIV-1 V3 Loop Consensus Motif Inhibit HIV-1 and HIV-2 Infection in CD4+ and CD4− Cells, Comptes Rendus De L'Academie Des Sciences, Serie III Sciences de la Vie, vol. 316, No. 11, 1993, pp. 1381-1387.
Savarino Andrea et al., Human CD38 Interferes with HIV-1 Fusion Through a Sequence Homologous to the V3 Loop of the Viral Envelope Glycoprotein gp120, FASEB Journal, vol. 17, No. 3, Mar. 2003, pp. 461-463.
Savarino Andrea et al., Human CD38 Interferes with HIV-1 Fusion Through a Sequence Homologous to the V3 Loop of the Viral Envelope Glycoprotein gp120, FASEB Journal Online, Jan. 22, 2003, pp. 1-20.
Yahi Nouara et al., Multibranched V3 Peptides Inhibit Human Immunodeficiency Virus Infection in Human Lymphocytes and Macrophages, Journal of Virology, The American Society for Microbiology, vol. 68, No. 9, Sep. 1994, pp. 5714-5720.
Jackson D.G., et al., Isolation of a Complementary DNA Encoding the Human CD38 T10 Molecule, a Cell Surface Glycoprotein with an Unusual Discontinuous Pattern of Expression During Lymphocyte Differentiation, Database NCBI Sep. 29, 1999, from NCBI Database Accession No. A43521.
Similarities in Amino Acid Sequences of Aplysia ADP-Ribosyl Cyclase and Human Lymphocyte Antigen CD38. TIBS, 1992, pp. 494-495.
Tohgo, et al., Essential Cysteine Residues for Cyclic ADP-ribose Synthesis and Hydrolysis by CD38. The Journal of Biological Chemistry, 1994, vol. 46, pp. 28555-28557.
Nata, Et al., Human Gene Encoding CD38 (ADP-ribosyl cyclase/ cyclic ADP-ribose hydrolase): Organization, Nucleotide Sequence and Alternative Splicing. GENE—An International Journal on Genes and Genomes, 1997, vol. 186, pp. 285-292.
Takasawa, Et al., Synthesis and Hydrolysis of Cyclic ADP-Ribose by Human Leukocyte Antigen CD38 and Inhibition of the Hydrolysis by ATP. The Journal of Biological Chemistry, 1993, vol. 268, pp. 26052-26054.

(Continued)

*Primary Examiner*—Jeffrey S. Parkin
(74) *Attorney, Agent, or Firm*—McCarter & English, LLP

(57) ABSTRACT

Peptides representing sequences from region 45-74 of the human CD38 leukocyte surface antigen (SEQ ID NO:1) are provided which may be used to inhibit or prevent transmission or replication of the HIV virus. The peptides have from 13 to 30 amino acids and include the amino acid sequence GPGTTK (SEQ ID NO:18) for topical application to inhibit or prevent transmission of the HIV virus.

7 Claims, 21 Drawing Sheets

OTHER PUBLICATIONS

Nakagawara, Et al., Assignment of CD38, the gene encoding human leukocyte antigen CD38 (ADP-ribosyl cyclase/cyclic ADP-ribose hydrolase), to chromosome 4p15. Cytogenet Cell Genet, 1995, vol. 69, pp. 38-39.

Jackson, Et al., Isolation of a cDNA Encoding the Human CD38 (T10) Molecule, A Cell Surface Glycoprotein with an Unusual Discontinuous Pattern of Expression During Lymphocyte Differentiation. The Journal of Immunology, 1990, vol. 144, pp. 2811-2815.

Yagui, Et al., A missense mutation in the CD38 gene, a novel factor for insulin secretion: association with Type II diabetes mellitus in Japanese subjects and evidence of abnormal function when expressed in vitro. Diabetologia, 1998, vol. 41, pp. 1024-1028.

Ferraro, Et al., Human CD38, a Leukocyte Receptor and Ectoenzyme, Is a Member of a Novel Eukaryotic Gene Family of Nicotinamide Adenine Dinucleotide$^+$-Converting Enzymes. The Journal of Immunology, 1997, pp. 3858-3865.

Savarino, Et al., Effects of the human CD38 glycoprotein on the early stages of the HIV-1 replication cycle. The FASEB Journal, 1999, vol. 13, pp. 2265-2276.

Savarino, Et al., Role of CD in HIV-1 infection: an epiphenomenon of T-cell activation or an acitve player in virus/host interactions? AIDS, 2000, vol. 14, pp. 1079-1089.

* cited by examiner

FIG. 1A

CD38    45RWRQTWSGPGTTKRFPETVLARCVKYTEIH
           :..  :::  . :   :  .    ..    ..:
gp120   299NTRKSHIGPG--RAFYTTGIIGDIR--QAH

FIG. 1B

```
          -----RWR-QTWSGPGTTKRFPETVLARCVKYTEIH
                       |V3 loop tip|
CladeB    TRPNNNTRKS-IIGPGRAFYTTGQIIGDIR---QAH
CladeA    TRPNNNTRRSIRIGPGQAFYATGDIIGDIR---QAH
CladeC    TRPNNNTRKSIRIGPGQTFYATGDIIGDIR---QAH
CladeD    TRPYNRQRT--PIGLGQAIYTTRYTTRIIG---QAY
CRF01AE   TRPSNNTRTS-RIGPGRVFYKTGDIIGDIR---KAY
Subgr.N   TRPGNNTGGQVQIGPAMTFYNIEKIVGDRQAY----
Subgr.O   -RPG----VQEIIGP-MAWYSMG--LNNSRAY----
SIV_CPZ   -RPGNNTRG--QIGPGMTFYNIENIVGDTRA-----
HIV_2     kRPGNKTVVPITLMSGLVFHS--QPINRPR---QAW

********************************  ***
          ******************************    ***
          *********  *******************    ***
          ******     *******************
                     ****************
```

Figure 7
A
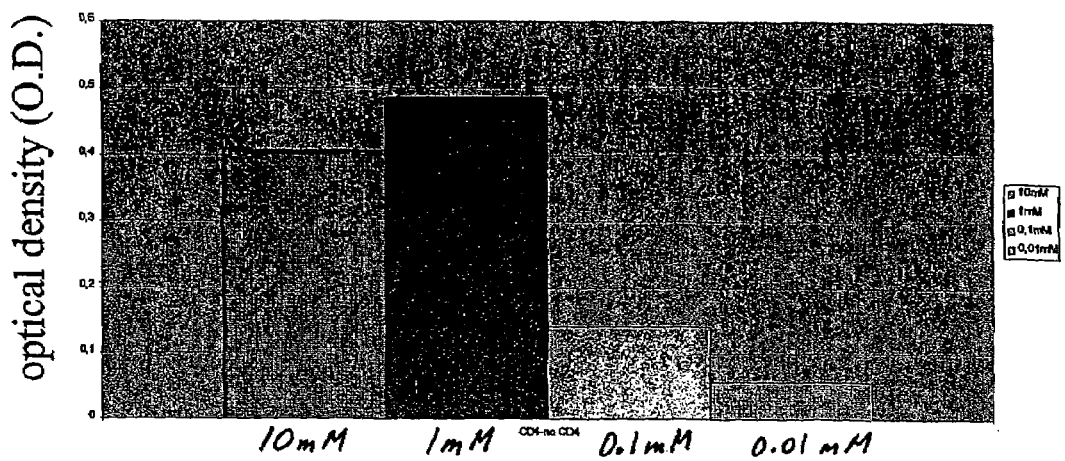
B
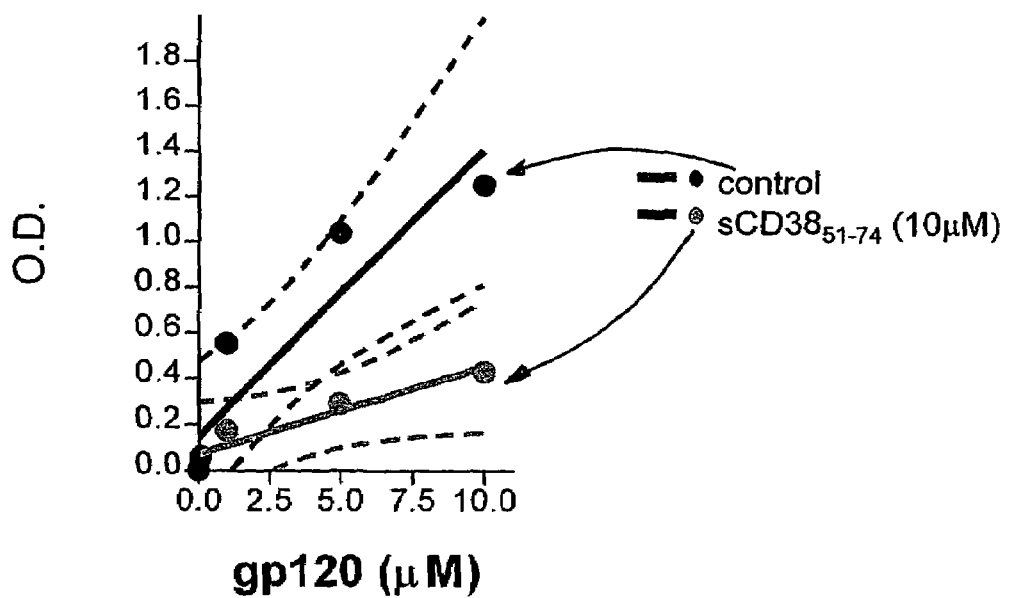

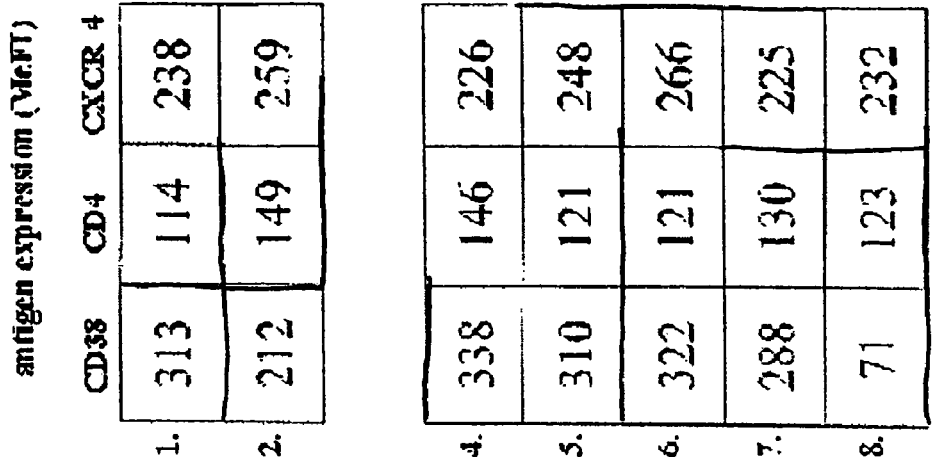
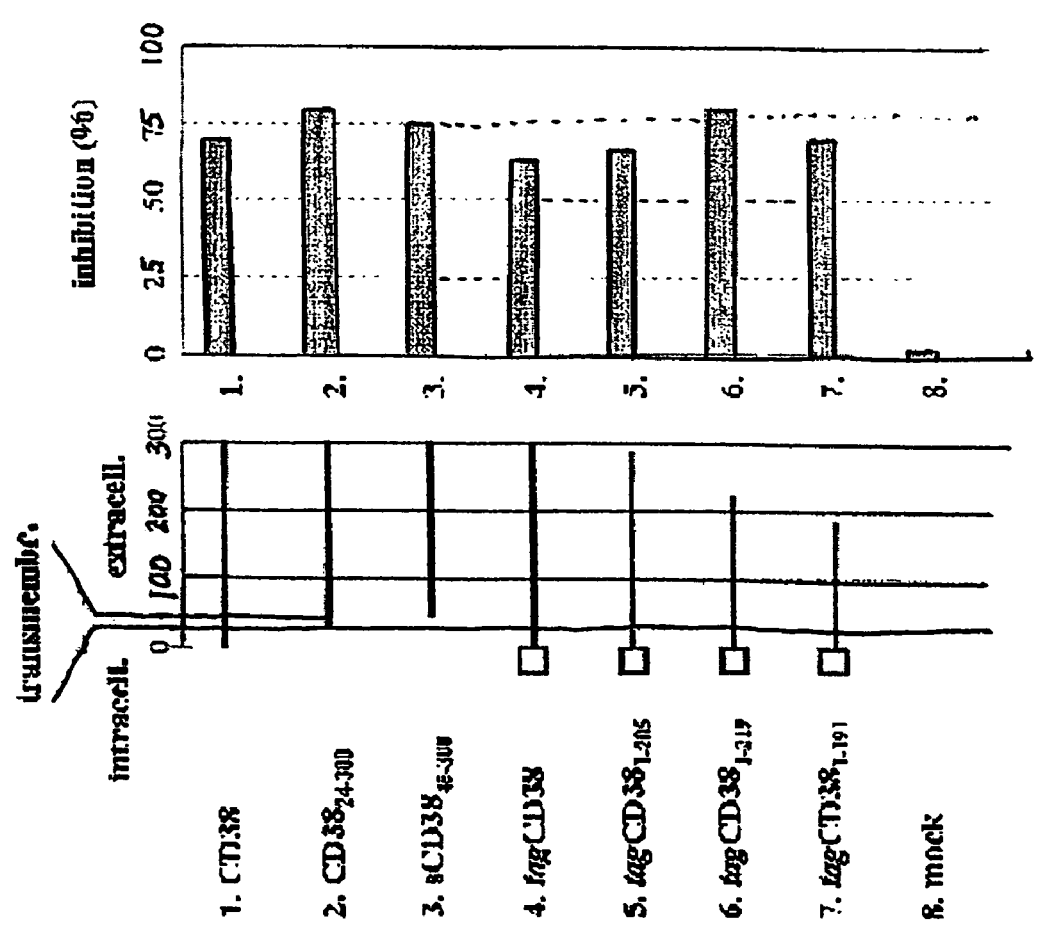

```
CD38    45RWRQQWSGPGTTKRFPETVLARCVKYTEIH
           :..  :::  .       ...      ..:
gp120  299NTRKSIIGPGRAFYTTGQIIG---DIRQAH
```

13 B

```
         -----RWR-QQWS GPGTTK RFPETVLARCVKYTEIH
                       |V3 loop tip|

CladeB   TRPNNNTRKS-II GPGRAF YTTGQIIGDIR---QAH
CladeA   TRPNNNTRRSIRI GPGQAF YATGDIIGDIR---QAH
CladeC   TRPNNNTRKSIRI GPGQTF YATGDIIGDIR---QAH
CladeD   TRPYNRQRT--PI GLGQAL YTTRYTTRIIG---QAY
CRF01AE  TRPSNNTRTS-RI GPGRVF YKTGDIIGDIR---KAY
Subgr.N  TRPGNNTGGQVQI GPAMTF YNIEKIVGDRQAY----
Subgr.O  -RPG----VQEII GP-MAW YSMG--LNNSRAY----
SIV_CPZ  -RPGNNTRG--QI GPGMTF YNIENIVGDTRA-----
HIV_2    kRPGNKTVVPITI MSGLVF HS--QPINRPR---QAW

******************************  ***
         ****************************    ***
         **********  *****************   ***
         ******       *****************
                      **************
```

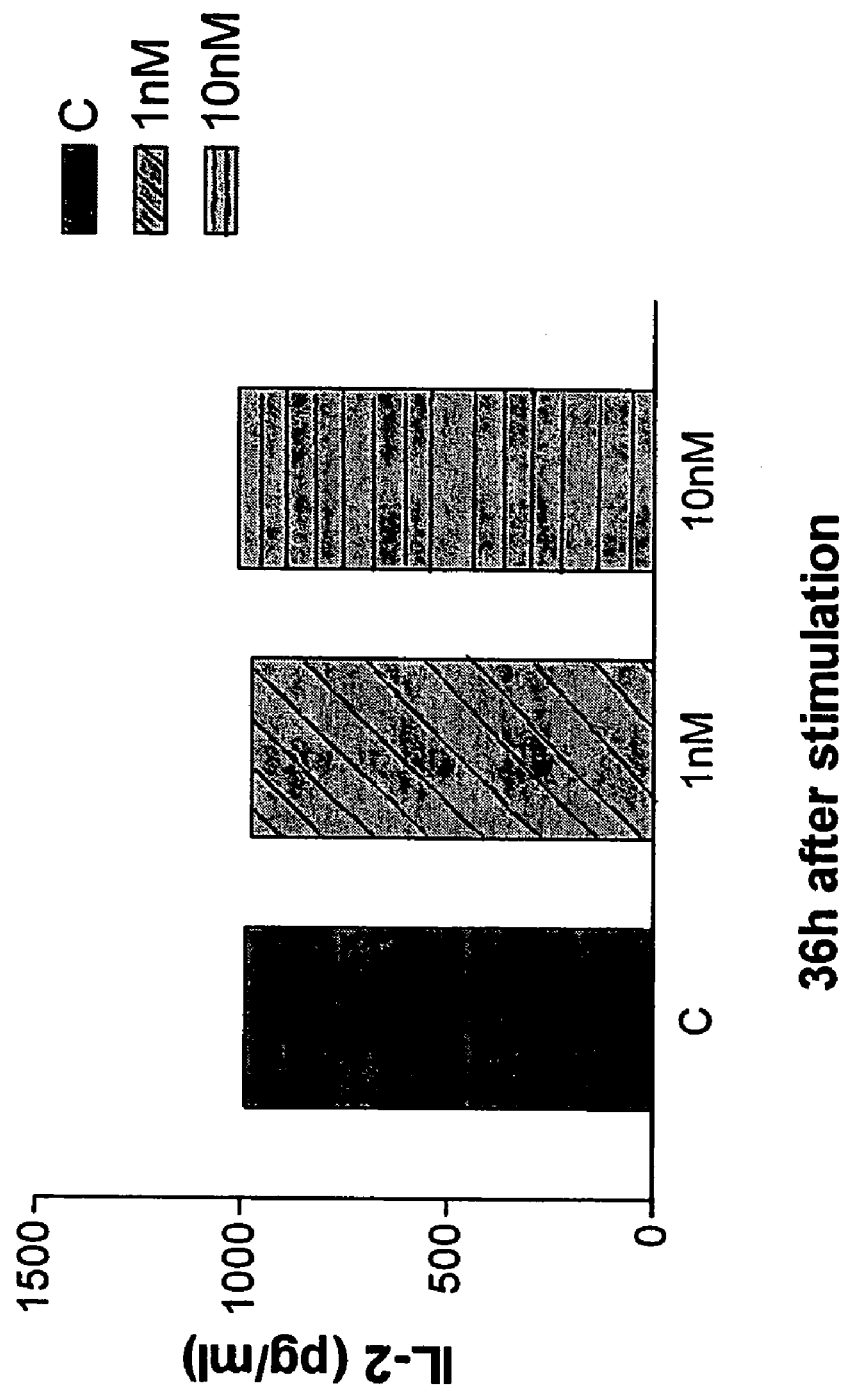

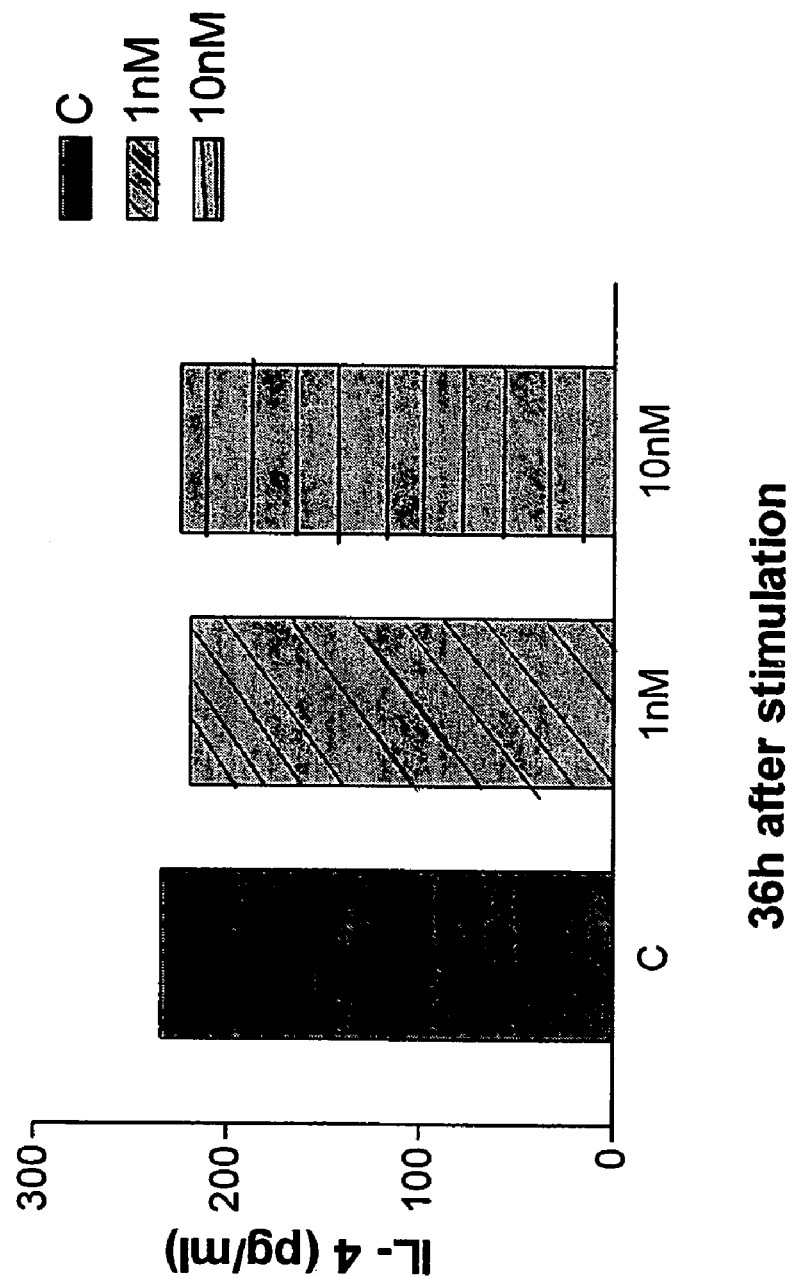

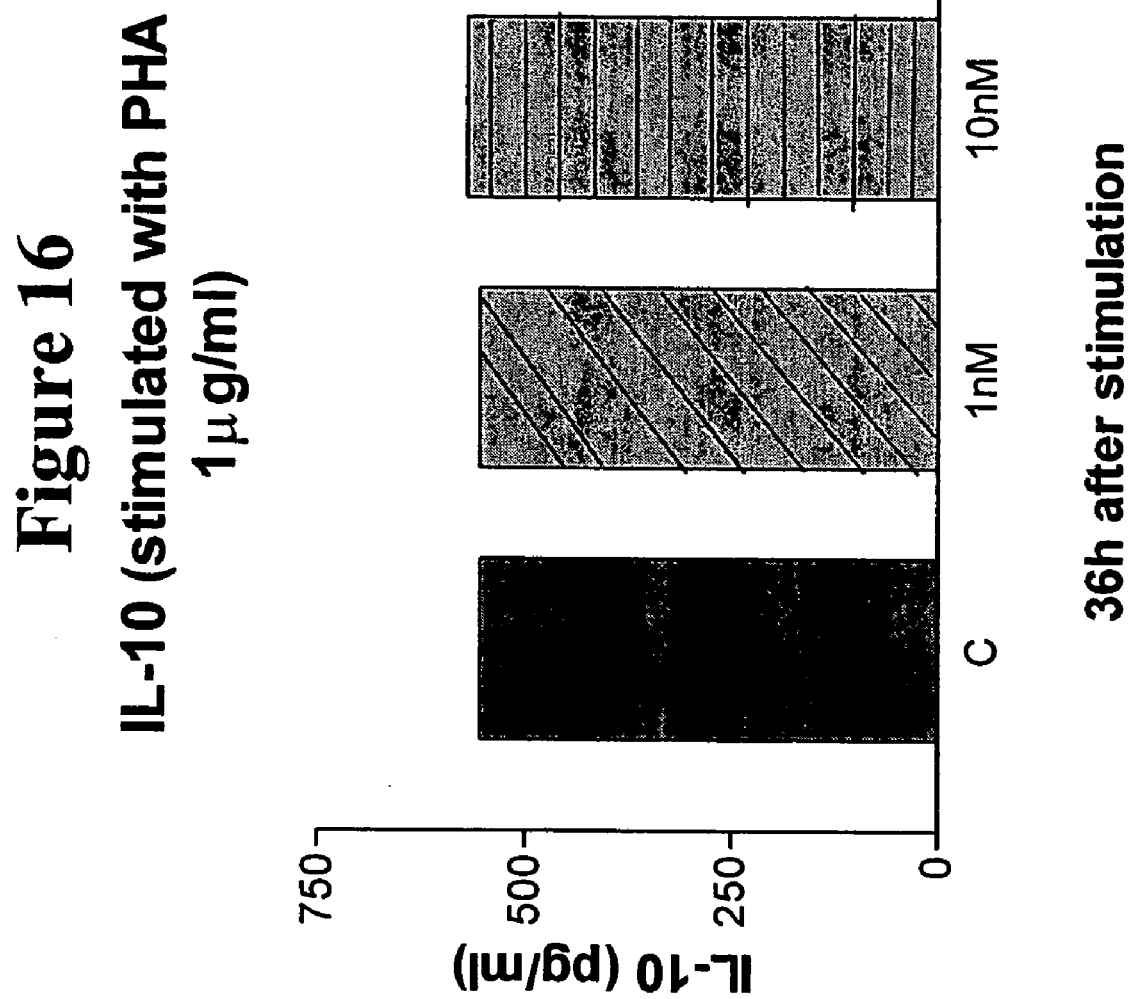

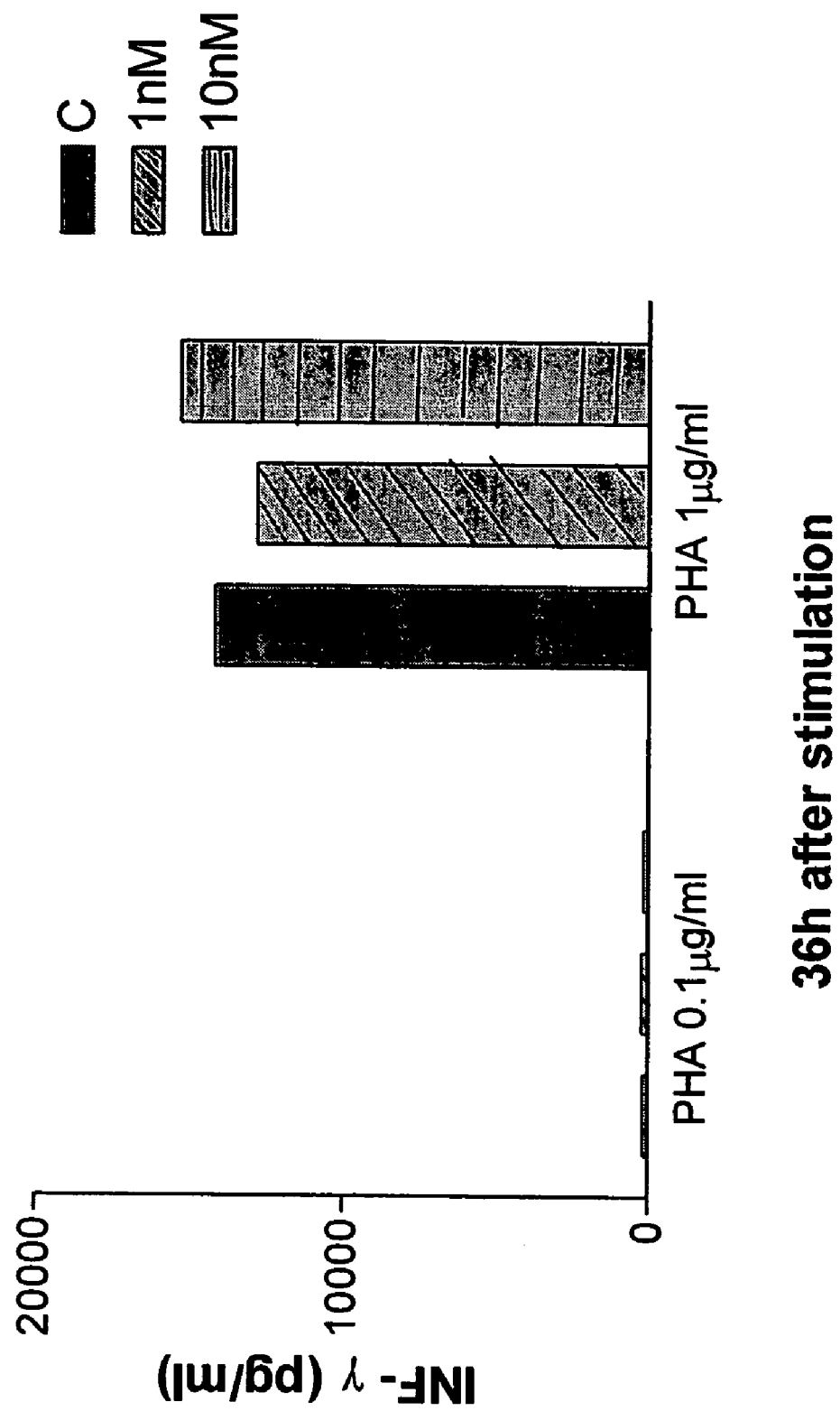

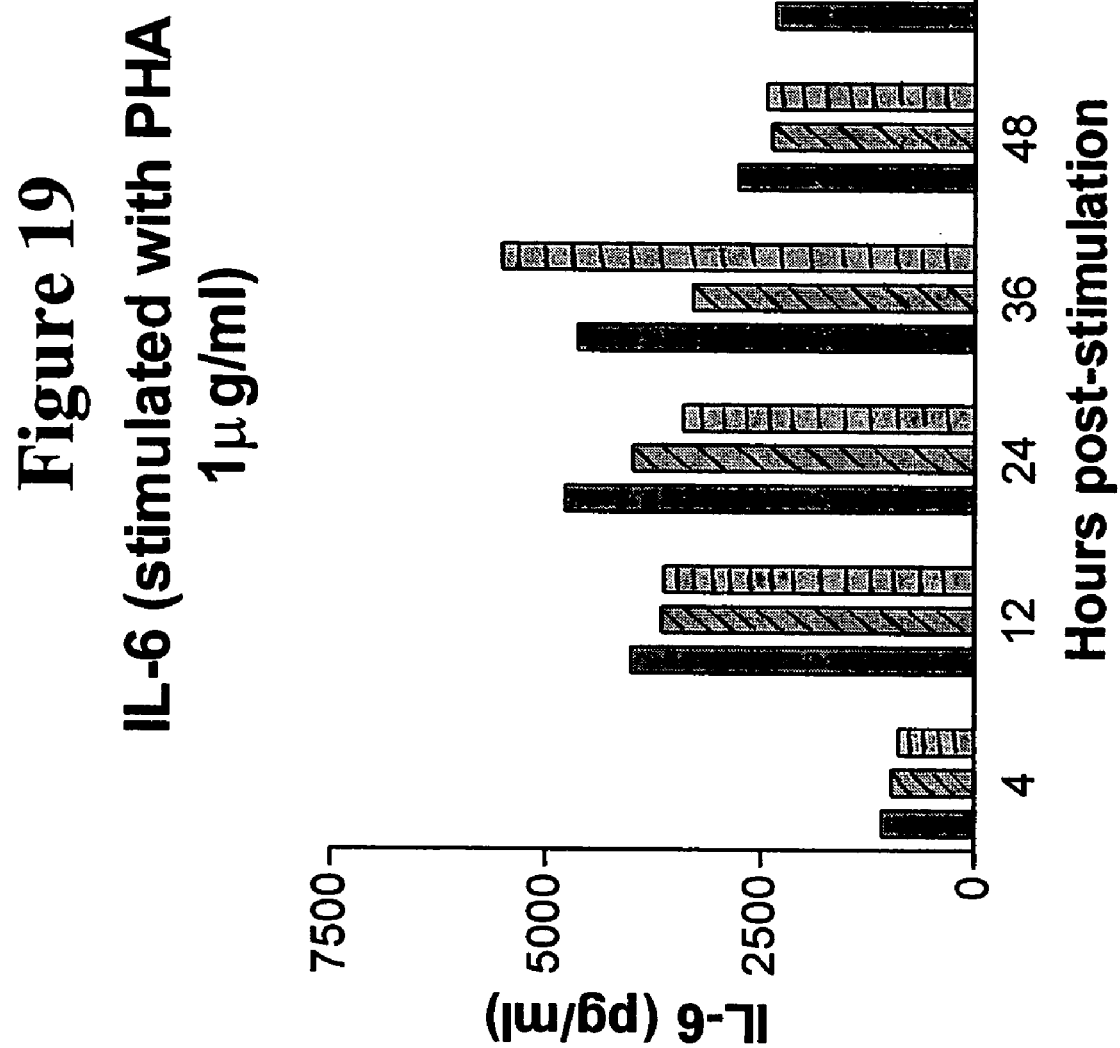

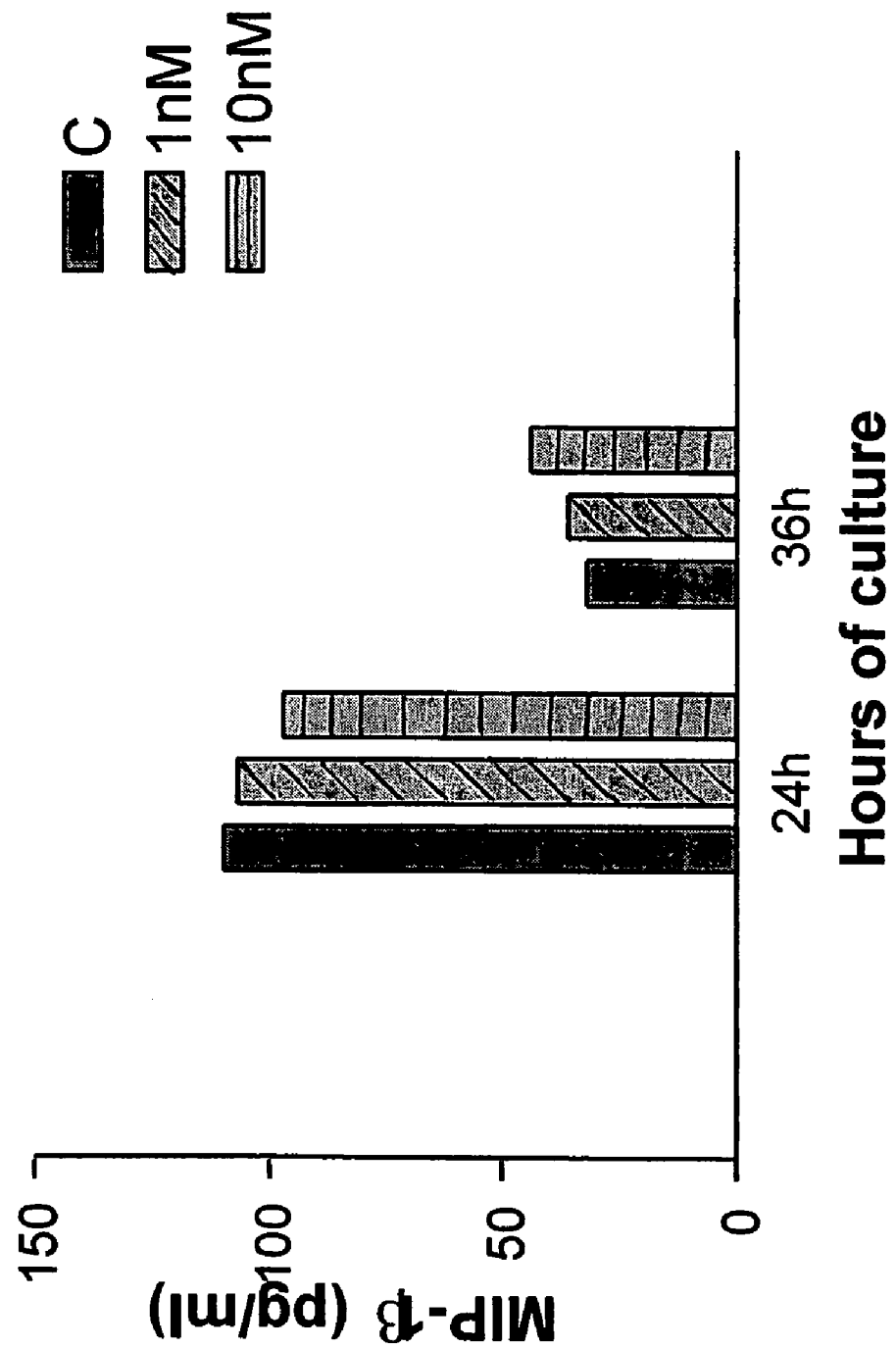

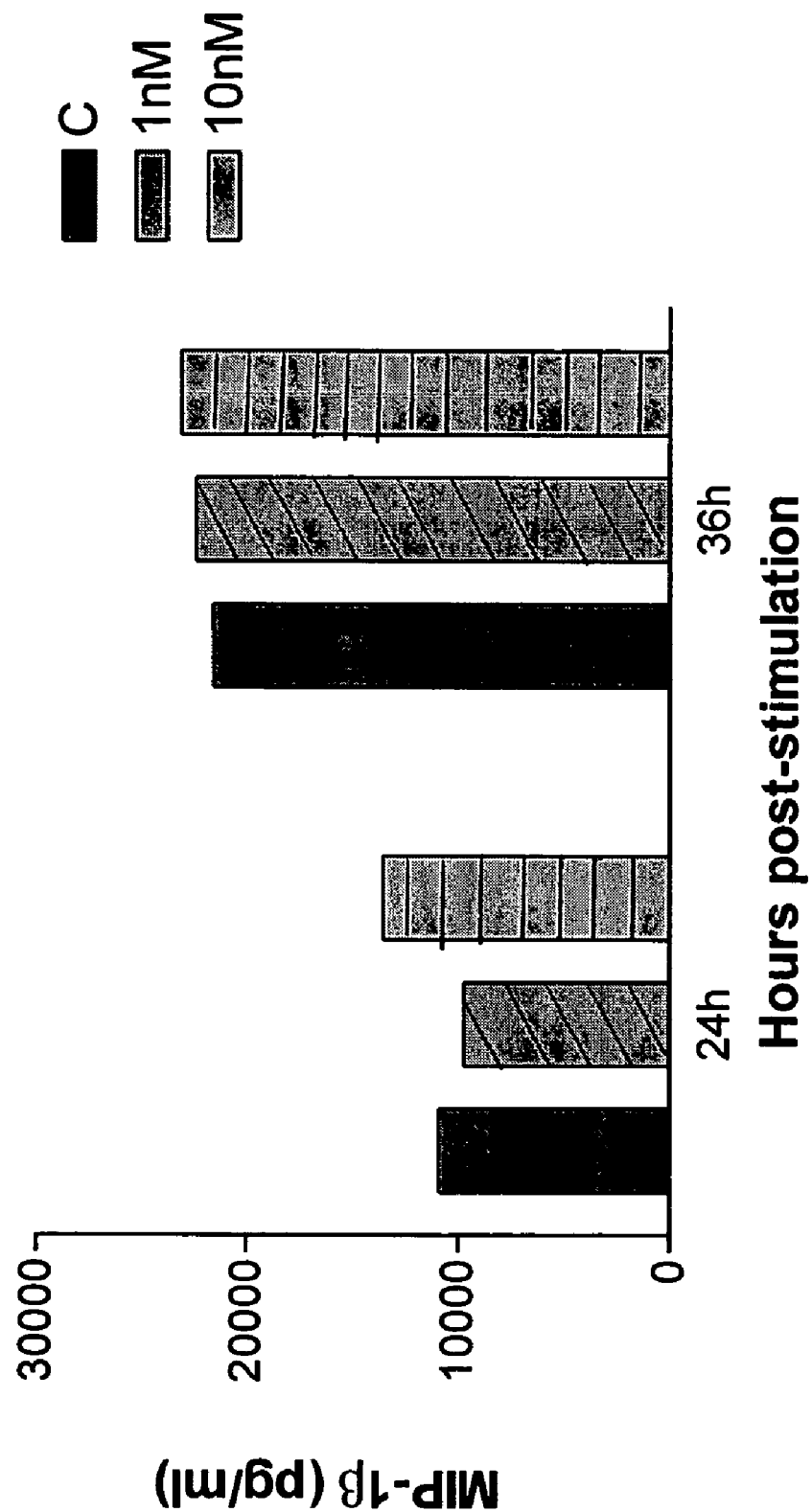

SEQUENCE LISTING

```
<160> NUMBER OF SEQ ID NOS: 22

<210> SEQ ID NO 1
<211> LENGTH: 30
<212> TYPE: PRT
<213> ORGANISM: Homo sapiens

<400> SEQUENCE: 1

Arg Trp Arg Gln Thr Trp Ser Gly Pro Gly Thr Thr Lys Arg Phe Pro
1               5                   10                  15

Glu Thr Val Leu Ala Arg Cys Val Lys Tyr Thr Glu Ile His
            20                  25                  30

<210> SEQ ID NO 2
<211> LENGTH: 26
<212> TYPE: PRT
<213> ORGANISM: Human immunodeficiency virus

<400> SEQUENCE: 2

Asn Thr Arg Lys Ser His Ile Gly Pro Gly Arg Ala Phe Tyr Thr Thr
1               5                   10                  15

Gly Ile Ile Gly Asp Ile Arg Gln Ala His
            20                  25
```

```
<210> SEQ ID NO 3
<211> LENGTH: 32
<212> TYPE: PRT
<213> ORGANISM: Human immunodeficiency virus

<400> SEQUENCE: 3

Thr Arg Pro Asn Asn Asn Thr Arg Lys Ser Ile Ile Gly Pro Gly Arg
1               5                   10                  15

Ala Phe Tyr Thr Thr Gly Gln Ile Ile Gly Asp Ile Arg Gln Ala His
            20                  25                  30

<210> SEQ ID NO 4
<211> LENGTH: 33
<212> TYPE: PRT
<213> ORGANISM: Human immunodeficiency virus

<400> SEQUENCE: 4

Thr Arg Pro Asn Asn Asn Thr Arg Arg Ser Ile Arg Ile Gly Pro Gly
1               5                   10                  15

Gln Ala Phe Tyr Ala Thr Gly Asp Ile Ile Gly Asp Ile Arg Gln Ala
            20                  25                  30

His

<210> SEQ ID NO 5
<211> LENGTH: 33
<212> TYPE: PRT
<213> ORGANISM: Human immunodeficiency virus

<400> SEQUENCE: 5

Thr Arg Pro Asn Asn Asn Thr Arg Lys Ser Ile Arg Ile Gly Pro Gly
1               5                   10                  15

Gln Thr Phe Tyr Ala Thr Gly Asp Ile Ile Gly Asp Ile Arg Gln Ala
            20                  25                  30

His

<210> SEQ ID NO 6
<211> LENGTH: 31
<212> TYPE: PRT
<213> ORGANISM: Human immunodeficiency virus

<400> SEQUENCE: 6

Thr Arg Pro Tyr Asn Arg Gln Arg Thr Pro Ile Gly Leu Gly Gln Ala
1               5                   10                  15

Leu Tyr Thr Thr Arg Tyr Thr Thr Arg Ile Ile Gly Gln Ala Tyr
            20                  25                  30

<210> SEQ ID NO 7
<211> LENGTH: 32
<212> TYPE: PRT
<213> ORGANISM: Human immunodeficiency virus

<400> SEQUENCE: 7

Thr Arg Pro Ser Asn Asn Thr Arg Thr Ser Arg Ile Gly Pro Gly Arg
1               5                   10                  15

Val Phe Tyr Lys Thr Gly Asp Ile Ile Gly Asp Ile Arg Lys Ala Tyr
            20                  25                  30

<210> SEQ ID NO 8
<211> LENGTH: 32
<212> TYPE: PRT
<213> ORGANISM: Human immunodeficiency virus
```

```
<400> SEQUENCE: 8

Thr Arg Pro Gly Asn Asn Thr Gly Gly Gln Val Gln Ile Gly Pro Ala
1               5                   10                  15

Met Thr Phe Tyr Asn Ile Glu Lys Ile Val Gly Asp Arg Gln Ala Tyr
            20                  25                  30

<210> SEQ ID NO 9
<211> LENGTH: 24
<212> TYPE: PRT
<213> ORGANISM: Human immunodeficiency virus

<400> SEQUENCE: 9

Arg Pro Gly Val Gln Glu Ile Ile Gly Pro Met Ala Trp Tyr Ser Met
1               5                   10                  15

Gly Leu Asn Asn Ser Arg Ala Tyr
            20

<210> SEQ ID NO 10
<211> LENGTH: 28
<212> TYPE: PRT
<213> ORGANISM: Human immunodeficiency virus

<400> SEQUENCE: 10

Arg Pro Gly Asn Asn Thr Arg Gly Gln Ile Gly Pro Gly Met Thr Phe
1               5                   10                  15

Tyr Asn Ile Glu Asn Ile Val Gly Asp Thr Arg Ala
            20                  25

<210> SEQ ID NO 11
<211> LENGTH: 31
<212> TYPE: PRT
<213> ORGANISM: Human immunodeficiency virus

<400> SEQUENCE: 11

Lys Arg Pro Gly Asn Lys Thr Val Val Pro Ile Thr Leu Met Ser Gly
1               5                   10                  15

Leu Val Phe His Ser Gln Pro Ile Asn Arg Pro Arg Gln Ala Trp
            20                  25                  30

<210> SEQ ID NO 12
<211> LENGTH: 30
<212> TYPE: PRT
<213> ORGANISM: Homo sapiens

<400> SEQUENCE: 12

Arg Trp Arg Gln Thr Trp Ser Gly Pro Gly Thr Thr Lys Arg Phe Pro
1               5                   10                  15

Glu Thr Val Leu Ala Arg Cys Val Lys Tyr Thr Glu Ile His
            20                  25                  30

<210> SEQ ID NO 13
<211> LENGTH: 28
<212> TYPE: PRT
<213> ORGANISM: Homo sapiens

<400> SEQUENCE: 13

Arg Gln Thr Trp Ser Gly Pro Gly Thr Thr Lys Arg Phe Pro Glu Thr
1               5                   10                  15

Val Leu Ala Arg Cys Val Lys Tyr Thr Glu Ile His
            20                  25
```

```
<210> SEQ ID NO 14
<211> LENGTH: 13
<212> TYPE: PRT
<213> ORGANISM: Homo sapiens

<400> SEQUENCE: 14

Arg Trp Arg Gln Thr Trp Ser Gly Pro Gly Thr Thr Lys
1               5                   10

<210> SEQ ID NO 15
<211> LENGTH: 24
<212> TYPE: PRT
<213> ORGANISM: Homo sapiens

<400> SEQUENCE: 15

Ser Gly Pro Gly Thr Thr Lys Arg Phe Pro Glu Thr Val Leu Ala Arg
1               5                   10                  15

Cys Val Lys Tyr Thr Glu Ile His
            20

<210> SEQ ID NO 16
<211> LENGTH: 30
<212> TYPE: PRT
<213> ORGANISM: Homo sapiens

<400> SEQUENCE: 16

Arg Trp Arg Gln Gln Trp Ser Gly Pro Gly Thr Thr Lys Arg Phe Pro
1               5                   10                  15

Glu Thr Val Leu Ala Arg Cys Val Lys Tyr Thr Glu Ile His
            20                  25                  30

<210> SEQ ID NO 17
<211> LENGTH: 28
<212> TYPE: PRT
<213> ORGANISM: Homo sapiens

<400> SEQUENCE: 17

Arg Gln Gln Trp Ser Gly Pro Gly Thr Thr Lys Arg Phe Pro Glu Thr
1               5                   10                  15

Val Leu Ala Arg Cys Val Lys Tyr Thr Glu Ile His
            20                  25

<210> SEQ ID NO 18
<211> LENGTH: 6
<212> TYPE: PRT
<213> ORGANISM: Homo sapiens

<400> SEQUENCE: 18

Gly Pro Gly Thr Thr Lys
1               5

<210> SEQ ID NO 19
<211> LENGTH: 30
<212> TYPE: PRT
<213> ORGANISM: Homo sapiens

<400> SEQUENCE: 19

Arg Trp Arg Gln Gln Trp Ser Gly Pro Gly Thr Thr Lys Arg Phe Pro
1               5                   10                  15

Glu Thr Val Leu Ala Arg Cys Val Lys Tyr Thr Glu Ile His
            20                  25                  30
```

```
<210> SEQ ID NO 20
<211> LENGTH: 27
<212> TYPE: PRT
<213> ORGANISM: Human immunodeficiency virus

<400> SEQUENCE: 20

Asn Thr Arg Lys Ser Ile Ile Gly Pro Gly Arg Ala Phe Tyr Thr Thr
1               5                   10                  15

Gly Gln Ile Ile Gly Asp Ile Arg Gln Ala His
            20                  25

<210> SEQ ID NO 21
<211> LENGTH: 23
<212> TYPE: PRT
<213> ORGANISM: Homo sapiens

<400> SEQUENCE: 21

Ser Gly Pro Gly Thr Thr Lys Arg Phe Pro Glu Thr Val Leu Ala Cys
1               5                   10                  15

Val Lys Tyr Thr Glu Ile His
            20

<210> SEQ ID NO 22
<211> LENGTH: 25
<212> TYPE: PRT
<213> ORGANISM: Homo sapiens

<400> SEQUENCE: 22

Lys Asn Ile Tyr Arg Pro Asp Lys Phe Leu Gln Cys Val Lys Asn Pro
1               5                   10                  15

Glu Asp Ser Ser Cys Thr Ser Glu Ile
            20                  25
```

COMPOSITIONS CONTAINING ANTI-HIV PEPTIDES AND METHODS FOR USE

CROSS-REFERENCE TO RELATED APPLICATIONS

This application claims priority to provisional application Ser. No. 60/375,105 filed on Apr. 23, 2002, provisional application Ser. No. 60/401,587 filed on Aug. 6, 2002, provisional application 60/428,734 filed on Nov. 23, 2002 and provisional application 60/441,346 filed on Jan. 20, 2003.

INCORPORATION BY REFERENCE

The present application hereby incorporates by reference, in its entirety, the Sequence Listing, and identical CRF of the Sequence Listing filed herewith. The CRF contains nucleotide and amino acid sequences, SEQ. ID NO. 1-28, in file: "SEQLIST_Savarino_Nov2006.ST25.txt"; created: 2 Nov. 2006; OS: MS Windows XP; Software: PatentIn v3.3; size: 14 KB. The information contained in the Sequence Listing submitted, herewith, in the instant application is identical to the sequence information contained in the computer readable form.

FIELD OF THE INVENTION

The present invention generally relates to peptides representing sequences from the human CD38 leukocyte surface antigen and therapeutic uses of those peptides. In particular, the present invention relates to peptides representing sequences from region 45-74 of the human CD38 leukocyte surface antigen and the use of these peptides for inhibition of HIV replication in vitro or in vivo.

BACKGROUND OF THE INVENTION

Highly active antiretroviral therapy (HAART) has markedly prolonged the survival of individuals infected with human immunodeficiency virus type 1 (HIV-1), but there exists an important need for intervention in the transmission of the virus itself. Indeed, there is a continual emergence of drug-resistant viruses, as well as a dramatic increase in the number of HIV-1 cases in resource-poor countries where the currently available therapies for HIV-1 infection are too expensive for wide spread use. Thus, there remains a need for the development of compositions and methods for the prophylactic treatment of HIV-1.

Current antiretroviral drugs inhibit the HIV-1 virus following its entry into cells. An important step forward in the fight against AIDS would be the availability of compositions capable of acting in the early events of virus replication, i.e., which would inhibit the fusion of the viral envelope with the plasma membrane of target cells. Drugs endowed with this characteristic activity are called "fusion inhibitors." Such drugs are being extensively sought in the effort to inhibit HIV-1 replication. As the events leading to HIV fusion are mediated by the viral envelope glycoproteins, these glycoprotein molecules represent the principal target for fusion inhibitors.

Fusion of the viral envelope of HIV with target cells consists of four steps: (1) primary interaction of the HIV envelope glycoprotein (gp120) with the human CD4 surface antigen, which acts as the principal HIV receptor; (2) conformational changes in both gp120 and CD4; (3) binding of gp120 to members of the chemokine-receptor family (CXCR-4 for the X4 HIV strains and CCR5 for the R5 strains), which act as HIV co-receptors; and (4) fusion between the cellular and viral membranes mediated by the gp41 viral envelope glycoprotein.

One strategy for fusion inhibition is to use peptides which mimic portions of the enveloping glycoproteins crucial for the early events in HIV replication. Peptides mimicking portions of the gp41 glycoprotein of HIV have shown in vitro anti-HIV activity and are currently being studied in clinical trials. One of them (T20, enfurtiuide) has recently been approved for use as a new anti-HIV drug in humans.

Another important target in the HIV envelope glycoproteins is the V3 loop of gp120, which is a crucial determinant for virus infectivity. The best described function of the V3 loop is its involvement in gp120 binding to chemokine receptors, but there are also data documenting the binding of the V3 loop to cell surface glycosphingolipids (GSL's) and CD4. Hammache, D., et al., "Specific interaction of HIV-1 and HIV-2 surface envelope glycoproteins with monolayers of galactosylceramide and ganglioside GM3," J Biol Chem, 273:7967-71 (1998); Benjouad, A., et al., "Multibranched peptide constructs derived from the V3 loop of envelope glycoprotein gp120 inhibit human immunodeficiency virus type 1 infection through interaction with CD4," Virology, 206:457-64 (1995). Interactions involving the V3 loop are described in U.S. Pat. No. 5,622,933 to Sabatier entitled "Multiple branch peptide constructions for use against HIV", which is incorporated herein in its entirety. The V3 loop appears to stabilize gp120 attachment to CD4 by binding, through its tip, the CDR3 region of the D1 domain of CD4, which is uninvolved in the primary interaction with gp120. Treatment strategies utilizing peptides from the V3 loop have been discouraging, however, due to the high degree of variation shown in the V3 sequences of the different HIV strains, and also by the high immunogenicity of these sequences.

The lack of available, effective vaccines has spawned interest in the topical administration of drug therapies, which would limit the sexual transmission of HIV, referred to herein as "topic microbiocides". Topic microbiocides would either kill the virus or, if the topic microbiocide belongs to the fusion inhibitor family, block entry of the virus into the body (not strictly a microbicidal action, but the term as used herein encompasses the inhibition action). The only therapy that has been extensively used for this purpose is nonxynol-9. A major drawback of this therapy, however, is that it can cause inflammation in the vaginal mucosa, therefore increasing rather than limiting HIV transmission. Other therapies have been postulated for this use as well. However, most of them are also likely to cause inflammation as they are derived from foreign tissues or sources. For these reasons, there is a need for a topic microbicide that inhibits HIV transmission without causing inflammation or toxic side effects. Such a therapy would greatly increase the safety of people who do not use condoms during sex, it would enhance the safety profile for those who do use condoms, and it could be used by women as a method of self-protection. In the search of topical microbicides with these characteristics, lessons can be learned from human proteins that are endowed with anti-HIV-1 effects.

Among the many proteins that are in some way associated with HIV-1 infection, the CD38 antigen merits particular consideration for use as an HIV-1 inhibitor due to its peculiar characteristics. Human CD38 is a type II surface glycoprotein with a molecular weight of 45 kD. As described in Savarino et al., "Role of CD38 in HIV-1 infection: an epiphenomenon of T-cell activation or an active player in virus/host interactions?", AIDS vol. 14, no. 9, 1079-89 (2000), the contents of which are hereby incorporated in their entirety, human CD38 is composed of a short intracytoplasmic tail, a single transmembrane region and a long extracellular domain. CD38 is thought to exert three functions on T cells: (1) as an ectoenzyme, it leads to the formation of cyclic ADP-ribose, a crucial compound in regulation of intracellular $Ca^{2+}$; (2) as an adhesion molecule, it mediates the interactions between leukocytes and vascular endothelial cells; and (3) as a molecule involved in transmembrane signaling, its engagement costimulates cell activation. In lymphocytes, surface CD38 has a peculiar pattern of expression, being expressed at high levels by recent thymic emigrants (RTE's), lost during maturation and re-expressed upon lymphocyte activation. Among T cells, it is detectable at high levels on mature thymocytes and activated T cells and at low levels on resting (i.e., HLA-$DR^-$-$CD25^-$-$CD69^-$) naive cells ($CD45RA^+$/$R0^-$ cells), whereas it is undetectable on resting memory cells ($CD45RA^-$/$R0^+$ cells).

The association between CD38 expression and lymphocyte activation makes CD38 a useful marker of progression in HIV disease, where generalized lymphocyte activation accompanies the progression of AIDS. Indeed, activation-related increases in CD38 molecules on both $CD8^+$ and $CD4^+$ T cells predict disease progression in HIV-1-infected adults. Conversely, decreased CD38 expression in both $CD8^+$ and $CD4^+$ T-cell subsets is a marker of effective response to HAART.

The available evidence indicates that there must be more to CD38 expression than its presence as an epiphenomenon of lymphocyte activation in HIV-1 infection. Indeed, CD38 is capable of interactions with some of the surface molecules involved in HIV-1 infection. The best documented of these interactions is the lateral association with CD4, the main HIV-1 receptor. Moreover, the CD38 molecule has been shown to be capable of interacting with cell surface GSL's. GSL's are organized in functional microdomains that have been compared to rafts moving on the plasma membrane. These rafts are associated with specific membrane proteins such as CD4. Recent studies suggest that GSL may also participate in HIV-1 fusion to $CD4^+$ cells. According to these studies, the GSL microdomain may help stabilize the attachment of the virus to CD4 through multiple low affinity interactions between the V3 domain of gp120 and the carbohydrate moiety of GSL. Interestingly, data developed by the present inventors and by others indicates that CD38 is preferentially expressed in membrane rafts.

Finally, the CD38 molecule may affect lymphocyte susceptibility to HIV-1 infection. Studies by the present inventors showed that CD38 expression was negatively correlated to susceptibility to HIV-1 infection in human lymphoid cell lines, and that transfection of CD38 into CD38-cells conferred partial resistance to replication of both laboratory-adapted HIV-1 strains and primary isolates. Savarino, A., et al., "Investigation of the potential role of membrane CD38 in protection against cell death induced by HIV-1," J Biol Regul Homeost Agents, 10:13-18 (1996); Savarino, A., et al., "Effects of the human CD38 glycoprotein on the early stages of the HIV-1 replication cycle", The FASEB Journal, 13:2265-2276, 1999. These observations are in line with in vivo studies of others reporting that most HIV-1 infected cells are $CD38^-$ in the early stages of infection in vivo, although the activated ($CD38^+$) portion of infected cells produce the highest levels of HIV-1 RNA. Zhang, et al., "Sexual transmission and propagation of SIV and HIV in resting and activated $CD4^+$ T cells", Science, 286:1353-1357 (1999). Based on this combined evidence, the present inventors recently published a model wherein HIV-1 gene expression displayed by some activated T cells would be due to post-entry events. Savarino, et al., "Role of CD38 in HIV-1 infection: an epiphenomenon of T-cell activation or an active player in virus/host interactions?", AIDS vol. 14, no. 9, 1079-89, 2000.

The present inventors evaluated the specificity and generality of the anti-HIV-1 effects of CD38 and defined the critical domains of the protein involved in its inhibitory effects. The inventors show that, in transfected MT-2 cells, CD38 is expressed in rafts and renders these cells partially resistant to HIV-1 fusion. The present invention relates to the CD38 down-modulation of gp120 attachment to CD4. These effects are not shared with other molecules interacting with CD4. Thus, using truncated forms of CD38, the present inventors identified a sequence reminiscent of the V3 loop of gp120 in the extracellular portion. Peptides containing this sequence replicated the effects of CD38 and inhibited X4 and R5 primary isolates from different HIV-1 subtypes without detectable toxicity. Conversely, deletion of the first six amino acids in the V3-like sequence abrogated HIV-1 inhibition by CD38. Accordingly, the present inventors have identified peptide sequences from the CD38 leukocyte surface antigen which can inhibit or limit HIV transmission, or inhibit HIV replication, in vitro or in vivo.

SUMMARY OF THE INVENTION

In one aspect, the invention provides novel compositions comprising a peptide or polypeptide representing amino acid sequences from region 45-74 (SEQ ID NO:1) of the human CD38 leukocyte surface antigen (SEQ ID NO:23) which are useful in inhibiting or limiting HIV transmission or HIV replication. The peptides or polypeptides may be included in a suitable pharmaceutical carrier for topical administration to inhibit or prevent transmission of HIV.

In another aspect, the present invention relates to methods of using the peptides or polypeptides representing amino acid sequences from region 45-74 (SEQ ID NO:1) of the human CD38 leukocyte surface antigen (SEQ ID NO:23) for therapeutic treatment of HIV infection. The present invention also relates to methods of using the peptides or polypeptides in compositions which may be used as local microbiocides as a prophylactic to prevent HIV infection in humans.

BRIEF DESCRIPTION OF THE DRAWINGS

FIGS. 1A and 1B show the sequence similarity between the membrane-proximal region of the human CD38 leukocyte surface antigen (SEQ ID NO:23) and the V3 loop of HIV-1 gp120.

FIG. 1A shows the alignment of the $CD38_{45-74}$ sequence (SEQ ID NO:1) with the consensus sequence for HIV-1 gp120 (SEQ ID NO:2) according to the LALIGN algorithm: local identities (:) and similarities (.).

FIG. 1B shows the alignment of the $CD38_{45-74}$ sequence (SEQ ID NO: 1) with consensus sequences for HIV-1 subtypes B (SEQ ID NO: 3), A (SEQ ID NO: 4), C (SEQ ID NO. 5), D (SEQ ID NO: 6), and E (SEQ ID NO: 7), groups N (SEQ ID NO: 8) and O (SEQ ID NO: 9), SIV_CPZ (SEQ ID NO: 10), and HIV-2 (SEQ ID NO: 11) according to Morgenstern's algorithm for multiple sequence alignment. The human $CD38_{45-74}$ sequence is used as a template to visualize its relationship with gp120 sequences representative of the diversity of the primate lentiviruses. The unaligned residues are shown in lower case. The number of '*' characters below the alignment reflects the degree of local similarity among sequences.

2A shows fluorescence resonance energy transfer (FRET) between CD4 and CD38 in MT-2 cells transfected with human CD38 (MT-2.CD38).

Figure 2:
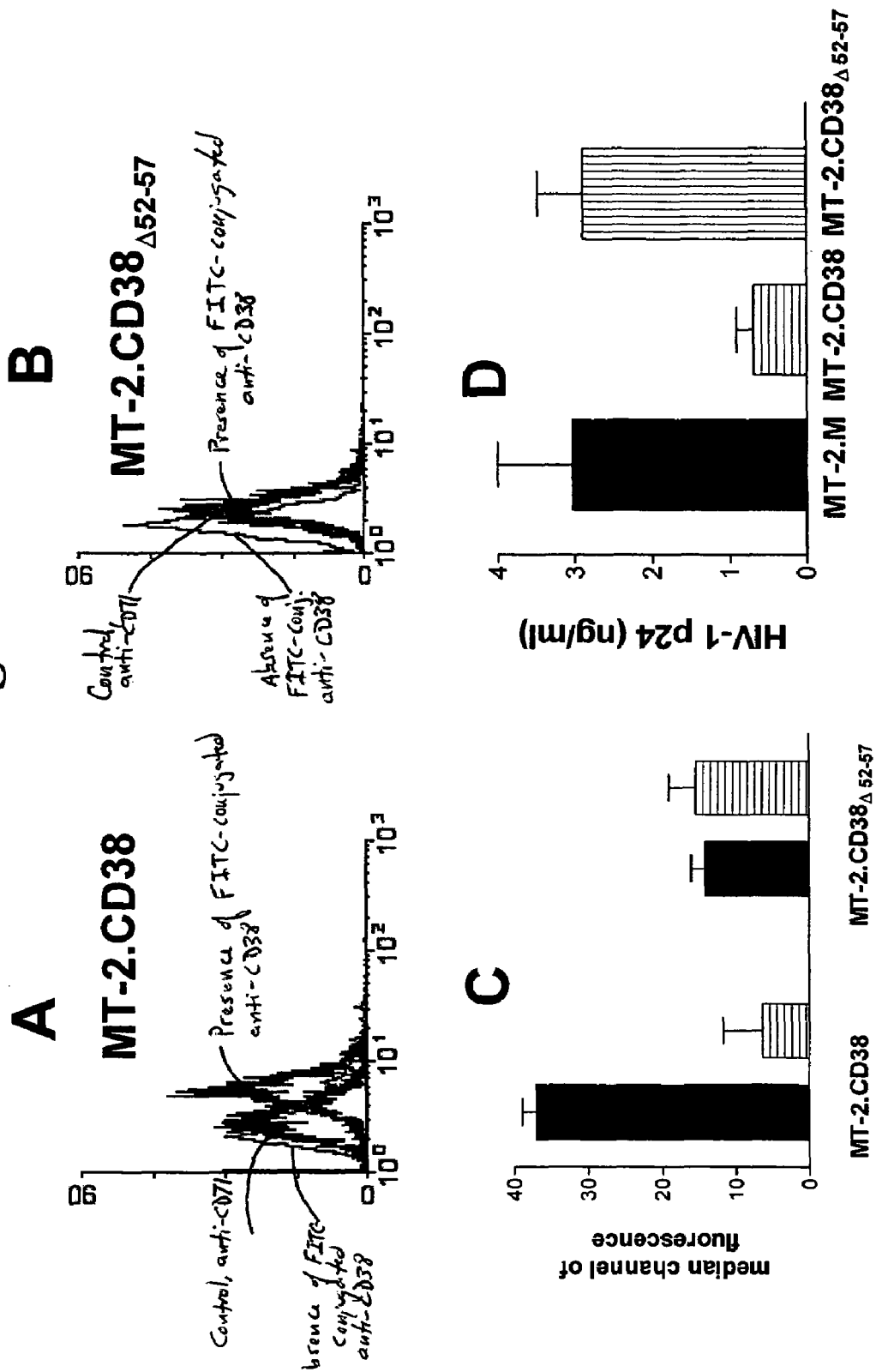
FIGS. 2A-2D show the effects of a CD38 molecule lacking the GPGTTK (SEQ ID NO: 18) hexamer ($CD38_{\Delta 52-57}$). FIG.

FIG. 2B shows FRET between CD4 and CD38$_{\Delta52\text{-}57}$ in MT-2 cells transfected with CD38$_{\Delta52\text{-}57}$ (MT-2. CD38$_{\Delta52\text{-}57}$). Cells were stained with Cy3-conjugated monoclonal antibodies (mAbs) to CD4 and FITC-conjugated mAbs to CD38 or to CD71.

In FIGS. 2A and 2B, FITC was excited at 488 nm and Cy3 emissions were collected at >600 nm. Each quadrant shows Cy3 emissions at >600 nm in the absence of FITC-conjugated anti-CD38 (black line) and in the presence of FITC-conjugated anti-CD38 (red line) or control anti-CD71 (blue line) mAbs. A right shift of the curve indicates FRET. The FACS profiles show one representative experiment.

FIG. 2C is a bar graph showing the mean ±S.D. of the median fluorescence intensities, expressed as median fluorescent channels, from 3 FRET experiments. (Solid bar is anti-CD38 mA, cross-hatched bar is anti-CD71 mAbs). CD38 displays FRET with CD38 but not with CD38$_{\Delta52\text{-}57}$ or with CD71 (Two-way ANOVA: P<0.01).

FIG. 2D is a bar graph showing p24 values in supernatants of de-novo HIV-1$_{IIIB}$-infected MT-2. CD38$_{\Delta52\text{-}57}$ and control MT-2.M cells at days 5 post-infection. HIV-1 replication in MT-2. CD38$_{\Delta52\text{-}57}$ cells (vertically-striped bars) was similar to that in MT-2.M cells (black bars) and higher than in MT-2.CD38 (horizontally-striped bars; *p<0.05, Student-Newman Keuls test following repeated-measures ANOVA). Results are presented as the means ±SEM. from three independent experiments.

Figure 3:
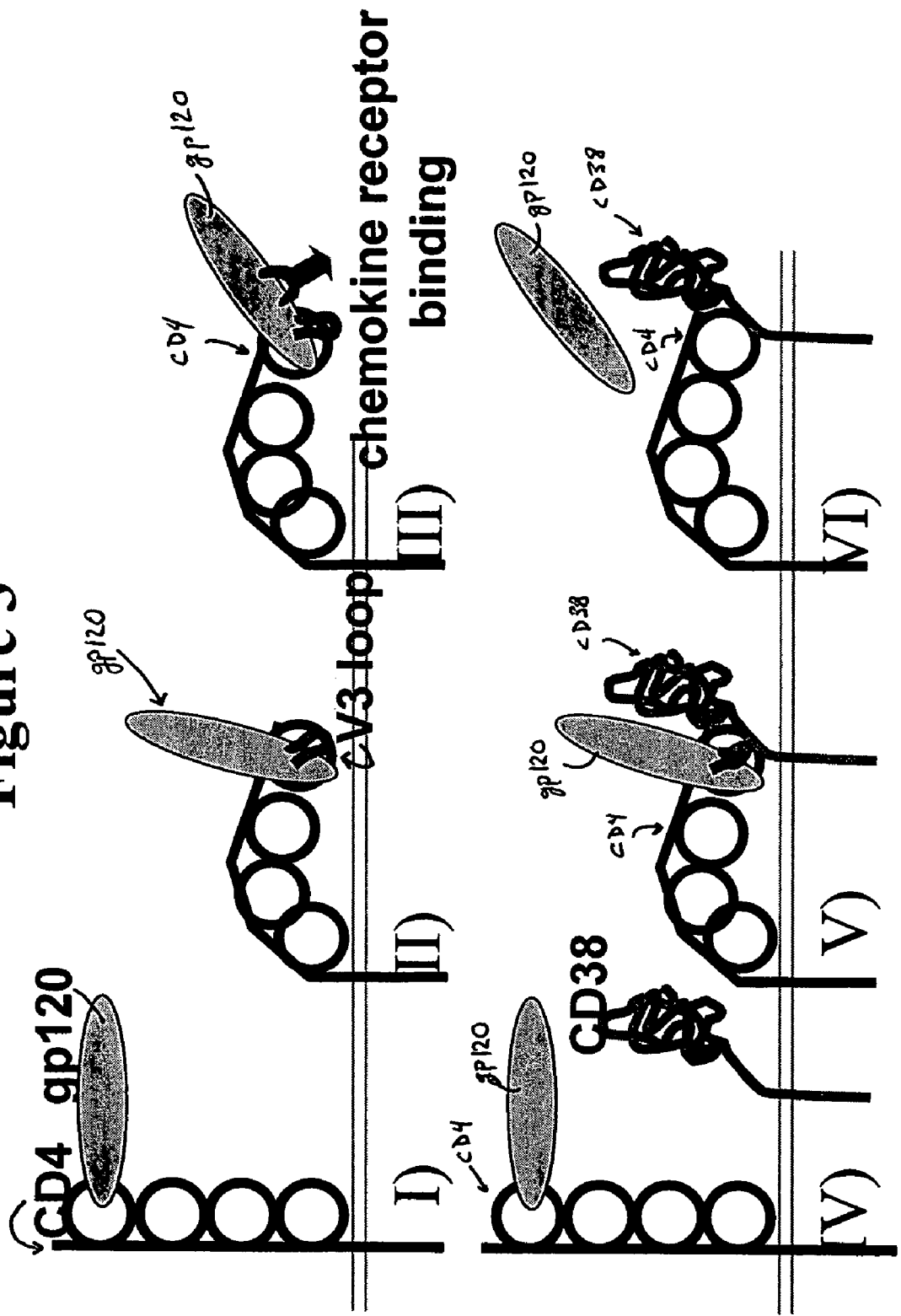

FIG. 3 is a representative depiction of the interplay between CD38 (SEQ ID NO:23), CD4 and gp120. Briefly, the very first step of HIV replication is a primary interaction between the CD4-binding site of gp120 and the CDR2 region of the D1 domain of CD4 (I). Although the precise sequence of events is to be clarified, there is evidence that, then the CD4 molecule folds (II) and (III) establishes, through the CDR3 region of the D1 domain, a second binding with the V3 loop of gp120. In the presence of CD38 (IV), the primary interaction between gp120 and CD4 would facilitate the CD4/CD38 interaction, thus counteracting the participation of the V3 loop to gp120/CD4 binding (V). The result would be down-modulation of gp120/CD4 binding (VI). For clarity, the molecules are not shown in proportion.

Figure 4:
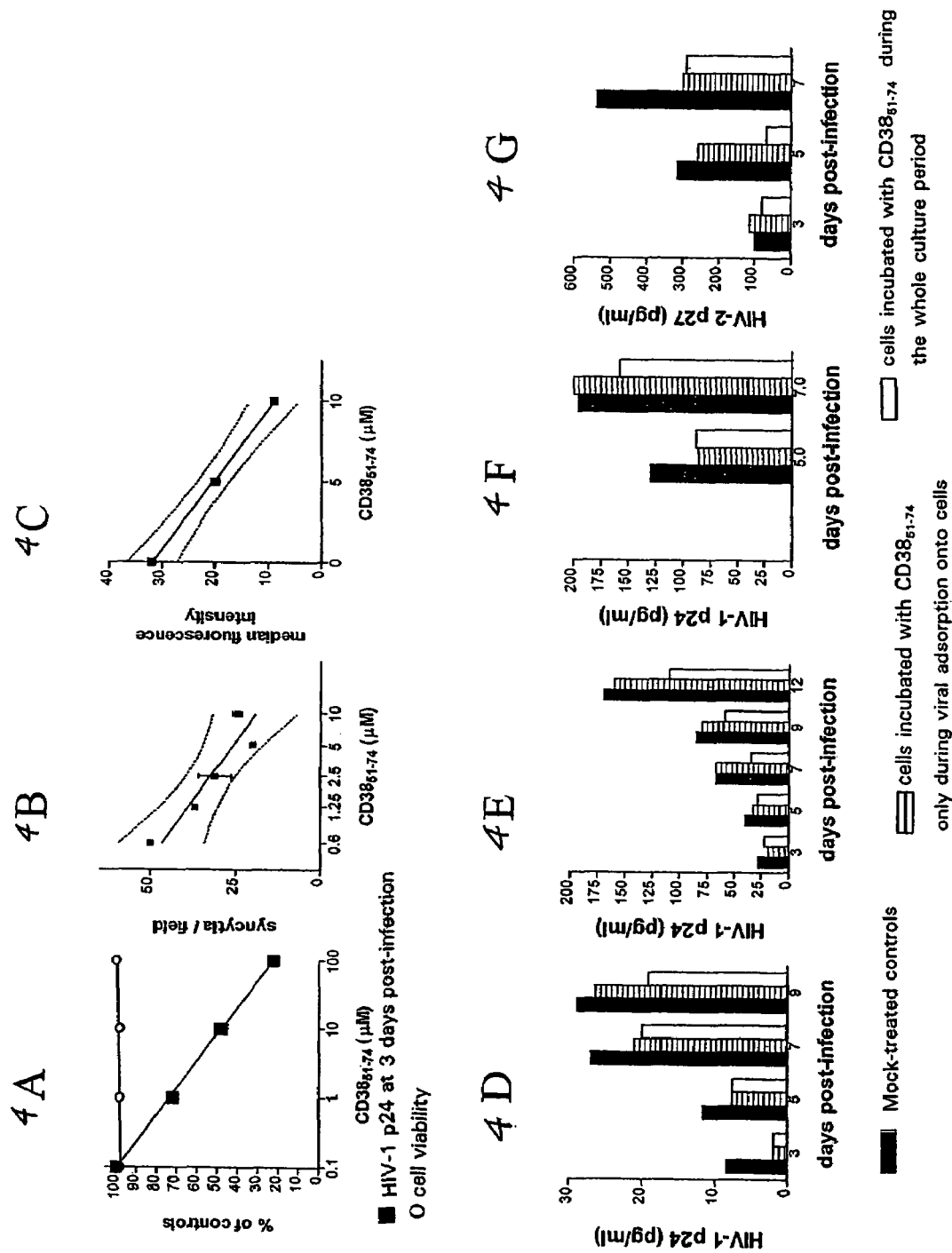

FIG. 4A shows a typical dose-dependent inhibition of HIV-1$_{IIIB}$ replication by the CD38$_{51\text{-}74}$ (SEQ ID NO:21) peptide in MT-4 cells. The straight line is the regression line best matching the p24 data points (t-test for slope: P<0.05)

FIG. 4B shows syncytium formation in MT-2/H9 IIIB co-cultures in the presence of different concentrations of CD38$_{51\text{-}74}$ (SEQ ID NO:21). The straight line is the regression line best matching the data points (t-test for slope: P<0.05). Dotted lines represent the 95% confidence limits of the regression line.

FIG. 4C shows staining of MT-4 cells with gp 120-fluorescein isothiocyanate (FITC) in the presence of CD38$_{51\text{-}74}$ (SEQ ID NO:21) (5 and 10 µM). The straight line is the regression line best matching the data points (t-test for slope: P<0.05). Dotted lines represent the 95% confidence limits of the regression line.

FIG. 4D shows inhibition of replication of a primary R5 isolate from HIV-1 Clade A in peripheral blood mononuclear cells (PBMC) incubated in the presence of s CD38$_{51\text{-}74}$ (SEQ ID NO:21) (10 µM). The upper limit of detection of the HIV-1 p24 antigen ELISA kit used is 200 pg/ml. Values from days 5, 7 and 9 were obtained by diluting 1:10 the cell culture supernatants.

FIG. 4E shows inhibition of replication of a primary R5 isolate from HIV-1 Clade D in PBMC incubated in the presence of CD38$_{51\text{-}74}$ (SEQ ID NO:21) (10 µM). Values from days 5, 7, 9 and 12 were obtained by diluting 1:10 the cell culture supernatants.

FIG. 4F shows inhibition of replication of a primary X4 isolate from HIV-1 Clade E in MT-4 cells incubated in the presence of CD38$_{51\text{-}74}$ (SEQ ID NO:21) (10 µM). The p24 values reported were obtained by diluting 1:1000 the cell culture supernatants.

FIG. 4G shows inhibition of replication of a primary R3/R5/X4 isolate from HIV-2 Clade A in MT-4 cells incubated in the presence of s CD38$_{51\text{-}74}$ (SEQ ID NO:21) (10 µM). The upper limit of detection of the HIV-2 p27 antigen ELISA kit used is 700 pg/ml. The p27 values of days 5 and 7 were obtained by diluting 1:10 the cell culture supernatants.

Figure 5:
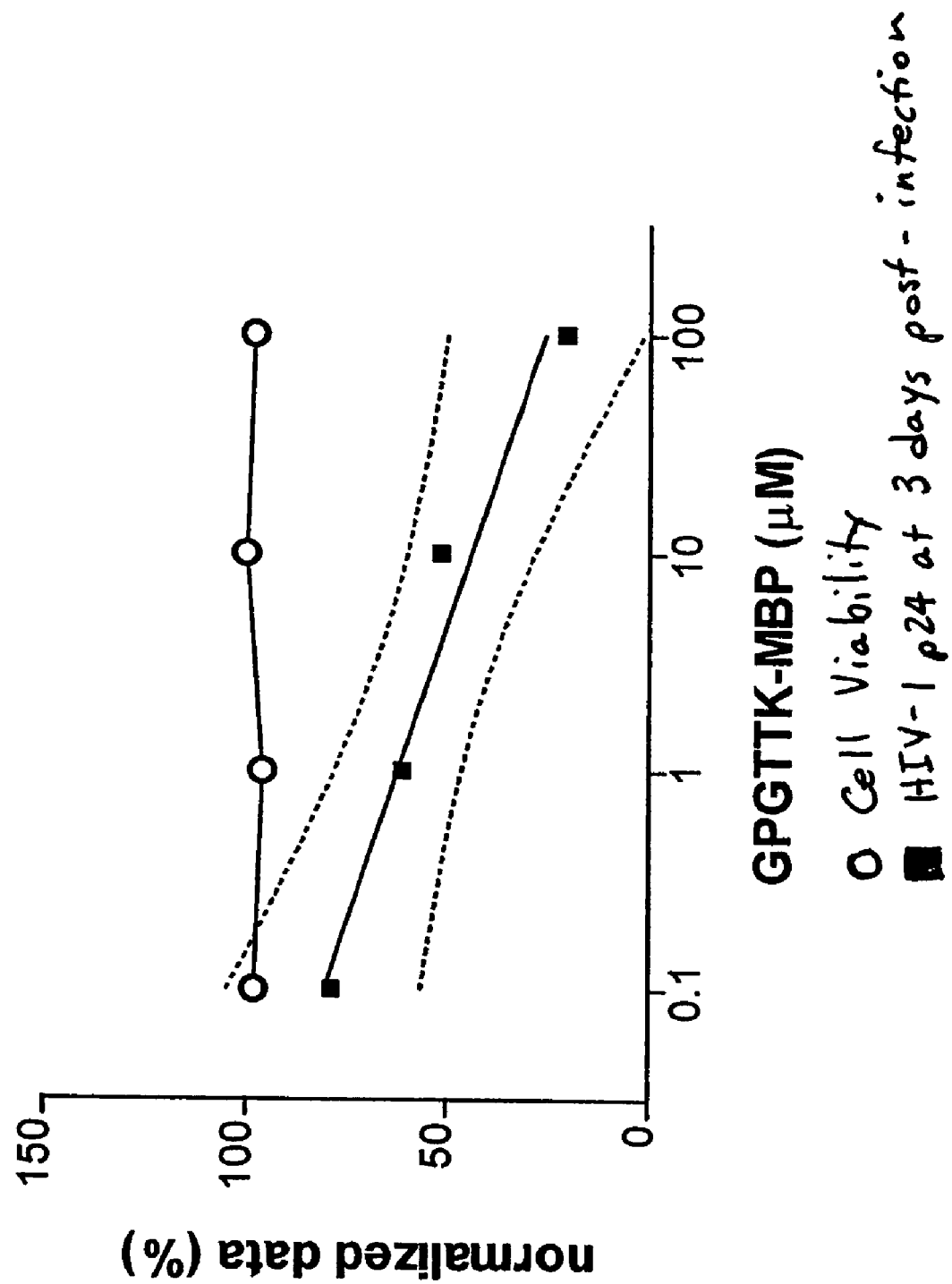

FIG. 5 shows a typical dose-dependent inhibition of HIV-1$_{IIIB}$ infection of MT-4 cells by an octameric branched peptide presenting the GPGTTK (SEQ ID NO: 18) sequence (GPGTTK MBP).

FIGS. 6A-6F show the effects of GPGTTK (SEQ ID NO: 18) MBP on HIV-1 cytopathogenicity in MT-4 cells.

FIG. 6A shows the appearance of a cluster of control, uninfected MT-4 cells.

FIG. 6B shows the appearance of a cluster of MT-4 cells at five days post-infection with HIV-1$_{IIIB}$.

FIG. 6C shows the appearance of a cluster of MT-4 cells at five days post-infection with HIV-1$_{IIIB}$ in the presence of GPGTTK (SEQ ID NO: 18) MBP (100 µM).

FIG. 6D shows "re-clustering" the MT-4 cells one hour after mechanical disruption of cell clusters.

FIG. 6E shows the impaired re-clustering of the MT-4 cells one hour after mechanical disruption of cell clusters.

FIG. 6F shows re-clustering of the MT-4 cells one hour after mechanical disruption of cell clusters.

FIG. 7A shows association of CD38-derived peptides to recombinant soluble human (rsh) CD4. On the x axis is the micromolar concentration of the peptide (biotinylated) utilized in the incubation mixture. On the y axis is the optical density (O.D.) obtained at the end of the reaction as described in Example III.

FIG. 7B shows down-modulation of recombinant HIV-1$_{IIIB}$ gp120 to rshCD4 by the CD38$_{51\text{-}74}$ (SEQ ID NO:21) peptide. On the x axis is the micromolar concentration of gp120 (biotinylated) utilized in the incubation mixture. On the y axis is the optical density (O.D.) obtained at the end of the reaction as described in Example 3. Straight lines represent regression lines; dotted lines represent 95% confidence limits of the regression lines. In black: regression line obtained by plotting different gp120 concentrations against the resulting O.D. values. In red the same in the presence of CD38$_{51\text{-}74}$ (SEQ ID NO:21). Regression lines were constructed on the basis of an average of data (reported in the graph) from three independent experiments.

Figure 8:
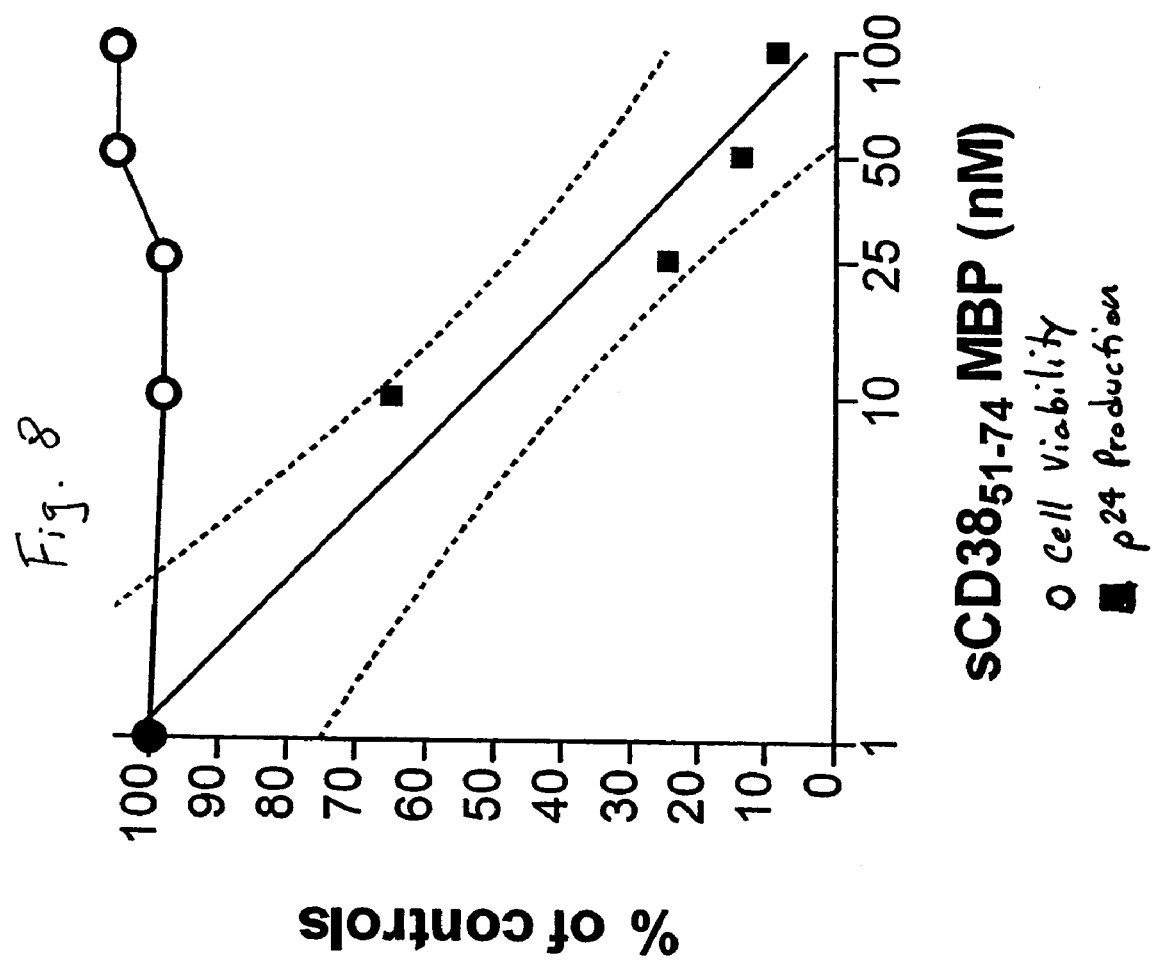

FIG. 8 shows the dose-dependent inhibition of HIV-1$_{IIIB}$ infection of MT-4 cells by sCD38$_{51\text{-}74}$ (SEQ ID NO:21)-MBP. Straight lines represent regression lines; dotted lines represent 95% confidence limits of the regression lines (p<0.01, t-test for slope). Data are representative of three independent experiments. Note that the concentrations of CD38$_{51\text{-}74}$ (SEQ ID NO:21) MBP on the x axis are reported on a logarithmic scale.

Figure 9:
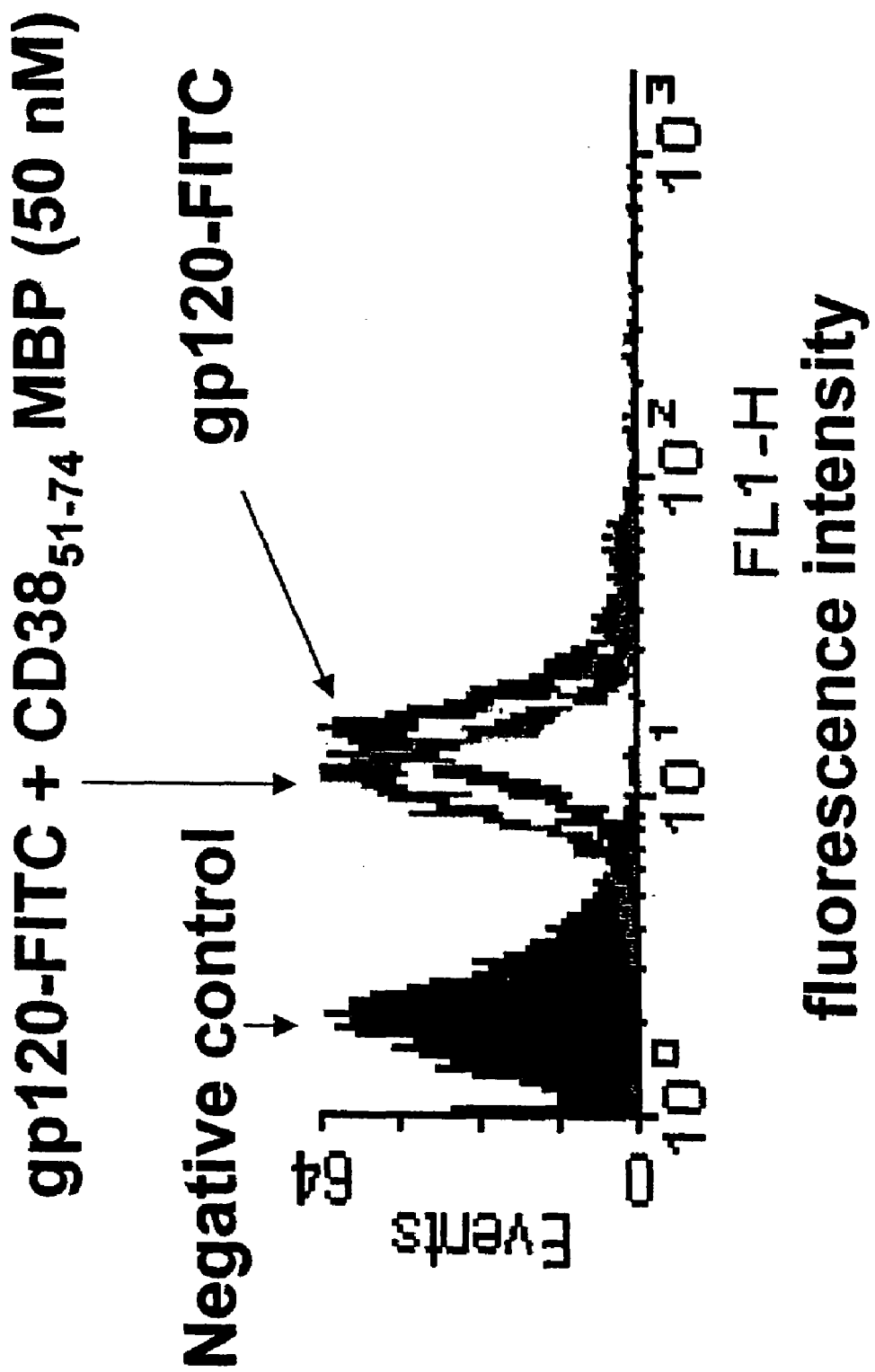

FIG. 9 shows down-modulation by CD38$_{51\text{-}74}$ (SEQ ID NO:21) MBP of fluorescein isothiocyanate (FITC)-labeled HIV-1 gp120 envelope glycoprotein binding to MT-2 cells. Results are presented as fluorescence histograms. The red curve shows the background fluorescence in the absence of gp120-FITC. The black/white curve shows the fluorescence of cells stained with gp120-FITC, and the green/white curve shows the fluorescence of cells stained with gp120-FITC in the presence of $CD38_{51-74}$ (SEQ ID NO:21) MBP, as indicated.

Figure 10:
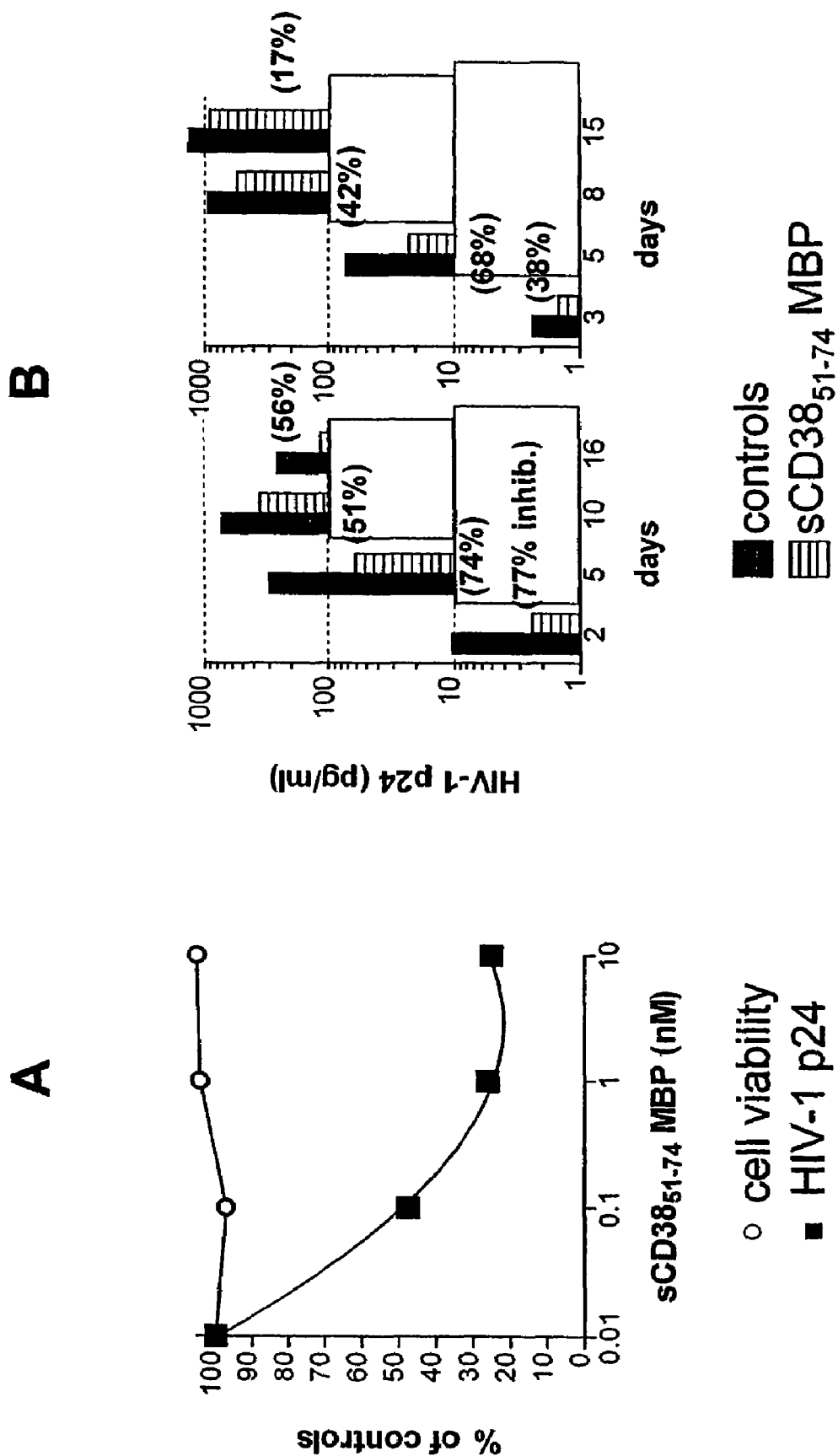

FIG. 10 shows effects of $CD38_{51-74}$ (SEQ ID NO:21) MBP on infection of PBMC by primary HIV-1 isolates. FIG. 10A shows the dose-dependent inhibition by $sCD38_{51-74}$ (SEQ ID NO:21)-MBP of infection of peripheral blood mononuclear cells (PBMC) with a primary R5 HIV-1 isolate (VI 829). Dose-dependence could be described as a polynomial second order curve, shown in the figure ($R^2=0.998$, non-linear regression). Cell viability was determined by the methyl tetrazolium (MTT) method, as described in Example V.

FIG. 10B shows the growth kinetics of two primary isolates (R5) belonging to subtype C (right: VI 829) and to subtype A (left: UG3) in PBMC infected in the presence (striped bars) or absence (black bars) of 1 nM $sCD38_{52-57}$ (SEQ ID NO: 18) MBP (the percentage of inhibition is shown in the brackets). The results using HIV-$1_{UG3}$ were obtained by inoculating cells at a multiplicity of infection (MOI) of 0.5, showing that $sCD38_{52-57}$ (SEQ ID NO: 18) MBP maintains the anti-HIV activity against a viral challenge higher than that usually adopted in our experiments (i.e., MOI=0.1).

Figure 11:
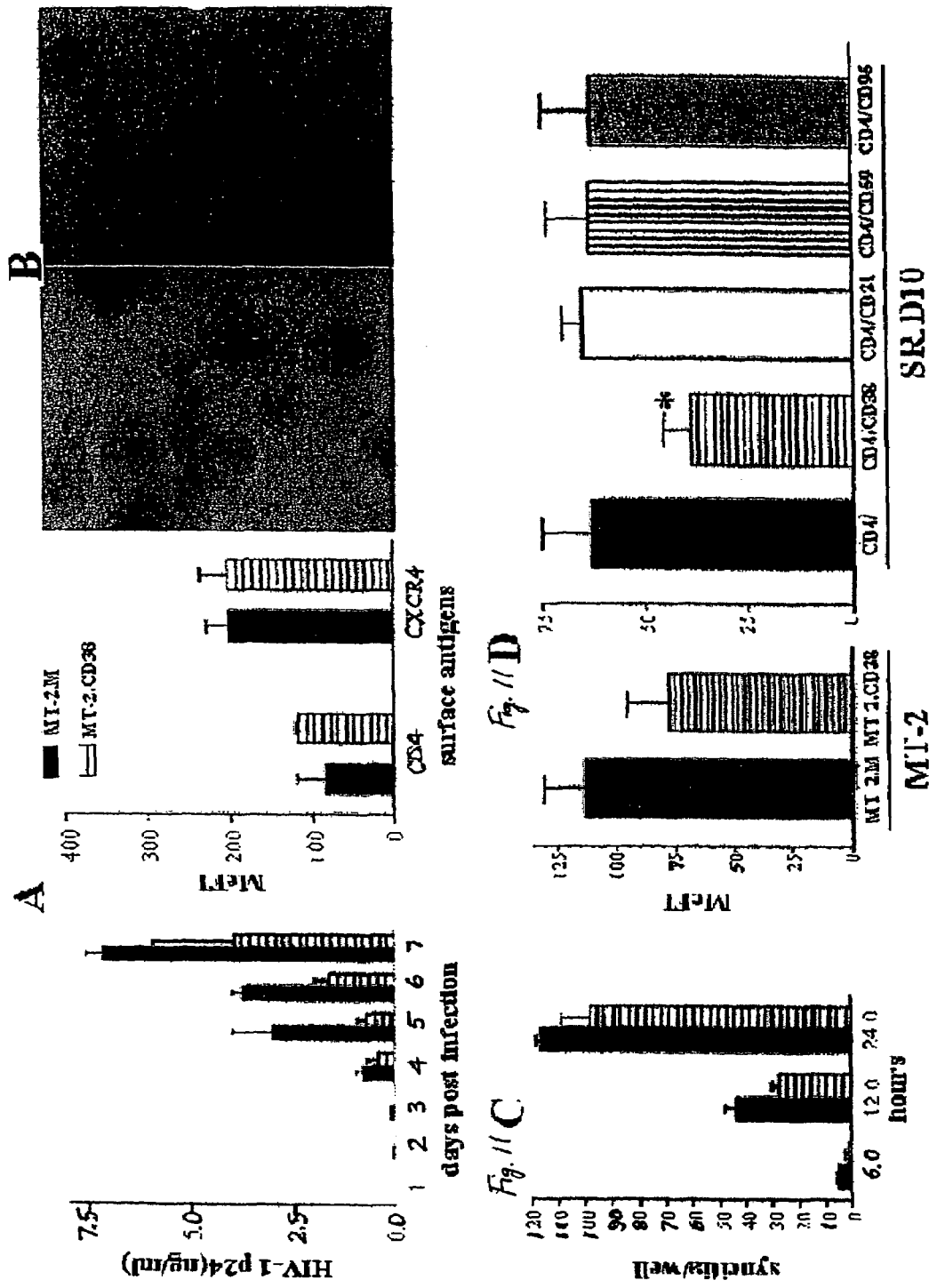

FIGS. 11A-D depict the effects of CD38 (SEQ ID NO:23) on the early stages of HIV-1 replication. FIG. 11A (Left): Production of HIV-1 p24 by mock-transfected MT-2 cells (MT-2.M; black bars) and CD38 transfectants (MT-2.CD38; striped bars) at different times after de-novo infection with HIV-$1_{IIIB}$. Results are presented as means ±SEM from two independent experiments (p<0.05, two-way ANOVA). (Right): Expression of CD4 and CXCR-4 in MT-2.M (black bars) and MT-2.CD38 (striped bars) cells. Results are presented as means ±SEM of the median fluorescence intensity (MeFI) from three experiments (CD4: p=0.50, CXCR-4: p=0.97, t-test for paired samples).

FIG. 11B Microphotographs (×100) showing syncytia in chronically-infected $H^9_{IIIB}$ cells co-cultivated for 12 hours with control MT-2.M cells (left) or MT-2.CD38 cells (right).

FIG. 11C shows quantification of syncytia in co-cultures of $H^9_{IIIB}$ cells with MT-2.M cells (black bars) or MT-2.CD38 cells (striped bars) at different times (means ±SEM, p<0.05 at 6 and 12 h, t-test for paired samples).

FIG. 11D shows binding of fluorescein isothiocyanate (FITC)-gp120 to MT-2 (left panel, black bars) and MT-2.CD38 (left panel, striped bars) cells (p<0.05, t-test for paired samples) and to murine SR.D10 cells transfected with human CD4 and selected surface receptors (right panel) (*p<0.05, Student-Newman-Keuls test following repeated-measures ANOVA). Fluorescence data from three experiments are shown as the means ±SEM of the MeFI. Panels C and D show results from three independent experiments.

FIGS. 12A-C show the effects of different portions of CD38 on HIV-1 replication. FIG. 12A is a schematic representation of the CD38 and CD38-derived molecules used in this study. In some cases, a myc-tag was added at the $NH_2$ terminus, since some of the truncated forms lacked the epitopes recognized by available mAbs.

FIG. 12B shows Inhibition of p24 production in de-novo HIV-$1_{IIIB}$-infected transfectants expressing full-length CD38 (SEQ ID NO:23 and 24) or truncated CD38 molecules including a soluble (s) form consisting solely of the extracellular domain ($sCD38_{45-300}$). Inhibition data were calculated on the basis of p24 levels in supernatants at day 5 after infection. Values represent medians from three experiments (ranges were <15% of the values reported). Data using mock-transfected cells (MT-2.M) are shown as a negative control. Values using a full-length tagCD38 show that the tag per se does not affect the inhibitory effects.

FIG. 12C shows staining for surface CD38, CD4 and CXCR-4 in MT-2-cell transfectants expressed as MeFI minus the negative control staining. Expression of tagged CD38 molecules was assessed with an anti-myc mAb; in this case the negative control staining was anti-myc staining of MT-2.M cells showing the basal staining of endogenous myc. The inhibitory effects on HIV-1 replication cannot be attributed to discrepancies in expression levels of CD4 and of CXCR-4, which were similar in all MT-2 clones transfected with the CD38-derived molecules and MT-2.M cells.

FIGS. 13A-B show alignment between CD38 and lentiviral envelope V3 loop sequences using a second published sequence of the membrane-proximal region of CD 38 (the NCBI RefSeq. accession number: D84276). FIG. 13A shows alignment of the $CD38_{45-74}$ sequence (SEQ ID NO: 19) with the consensus sequence for HIV-1 subtype B (SEQ ID NO: 20) according to the LALIGN software.

FIG. 13B shows alignment of the $CD38_{45-74}$ sequence (SEQ ID NO. 19) with consensus sequences for HIV-1 sub-types B (SEQ ID NO: 3), A (SEQ ID NO: 4), C (SEQ ID NO. 5), D (SEQ ID NO: 6), and E (SEQ ID NO: 7), groups N (SEQ ID NO: 8) and O (SEQ ID NO: 9), SIV_CPZ (SEQ ID NO: 10), and HIV-2 (SEQ ID NO: 11) according to Morgenstern's DIALGN algorithm for multiple sequence alignment (http://www.expasy.ch). The human $CD38_{45-74}$ sequence is used as a template to visualize its relationship with gp120 sequences representative of the diversity of the primate lentiviruses. In B, the unaligned residues are shown in lower case. The number of asterisks below the alignment reflects the degree of local similarity among sequences. The area of highest similarity includes the V3 loop tip (boxed area). The NCBI RefSeq accession number for human CD38 is D84276.

FIGS. 14, 15, 16 and 17 depict the results of one out of three experiments with essentially identical results. FIG. 14 shows the effects of $CD38_{51-74}$ (SEQ ID NO:21) MBP (1 and 10 nM) on the levels of interleukin(IL)-2 in peripheral blood mononuclear cells (PBMC) stimulated with 1 microg/ml phytohemoagglutinin (PHA).

FIG. 15 shows the effects of $CD38_{51-74}$ (SEQ ID NO:21) MBP (1 and 10 nM) on the levels of IL-4 in PBMC stimulated with 1 microgram/ml PHA.

FIG. 16 shows the effects of $CD38_{51-74}$ (SEQ ID NO:21) MBP (1 and 10 nM) on the levels of IL-10 in PBMC stimulated with 1 microgram/ml PHA.

FIG. 17 shows the effects of $CD38_{51-74}$ (SEQ ID NO:21) MBP (1 and 10 nM) on the levels of interferon(IFN)-alpha in PBMC stimulated with PHA (0.1 and 1 microgram/ml).

FIGS. 18A and B show the effects of $CD38_{51-74}$ (SEQ ID NO:21) MBP (1 and 10 nM) on the levels on the levels of tumor necrosis factor (TNF)alpha in PHA-stimulated PBMC of two donors showing different responses.

FIG. 19 shows the effects of $CD38_{51-74}$ (SEQ ID NO:21) MBP (1 and 10 nM) on the levels of IL-6 in PBMC at different intervals post-stimulation with PHA (1 microgram/ml). The donor is the same as in FIGS. 18A/19A.

FIGS. 20 and 21 depict the results of one out of three experiments with essentially identical results. FIG. 20 shows the effects of $CD38_{51-74}$ (SEQ ID NO:21) MBP (1 and 10 nM) on the levels of macrophage-inflammatory protein (MIP)-1beta in non-stimulated PBMC.

FIG. 21 shows the effects of $CD38_{51-74}$ (SEQ ID NO:21) MBP (1 and 10 nM) on the levels of MIP-1beta in PBMC at different intervals post-stimulation with PHA (1 microgram/ml).

DETAILED DESCRIPTION OF THE INVENTION

The present invention relates to peptides representing sequences from region 45-74 of the human CD38 leukocyte surface antigen (SEQ ID NO:1) and the use of these peptides as inhibitors of HIV replication.

A GPG amino acid motif is present in both CD38 and gp120. In gp120, the GPG amino acid motif occurs in the V3 loop. In CD38 (SEQ ID NO:23), the motif occurs in the membrane-proximal portion of the extracellular domain, as described by Jackson and Bell. Jackson, D. G., and Bell, J. I., "Isolation of a cDNA encoding the human CD38 (T10) molecule, a cell surface glycoprotein with an unusual discontinuous pattern of expression during lymphocyte differentiation," J Immunol 144:2811-2815 (1990). This triplet is highly conserved in the different HIV-1 strains and is considered to be an important determinant for infectivity.

As illustrated in FIG. 1A, sequence comparison between the V3 loop of HIV-1 gp120 (SEQ ID NO:2) and the first 30 amino acids of CD38 outside the plasma membrane (amino acids 45-74, i.e. $CD38_{45-74}$ (SEQ ID NO:1)) shows that $CD38_{45-74}$ has approximately 50% similarity with a large portion of the V3 loop of HIV-1. Most identities and similarities were found at the level of those amino acids that are highly conserved among the different HIV-1 subtypes. The generality and specificity of this similarity can be shown by performing a multiple alignment between $CD38_{45-74}$ (SEQ ID NO:1) and the V3 loop consensus sequences for the principal HIV-1 group M subtypes (B (SEQ ID NO:3), A (SEQ ID NO:4), C (SEQ ID NO:5), D (SEQ ID NO:6), and $CRF_{01}$ AE (SEQ ID NO:7)), for HIV-1 groups N (SEQ ID NO:8) and O (SEQ ID NO:9), for SIV_cpz (the common ancestor of the HIV-1 groups) (SEQ ID NO:10), and for HIV-2 (SEQ ID NO:11). As shown in FIG. 1B, using Morgenstern's DIALIGN algorithm (Morgenstern et al., Bioinformatics, 1998), it can be seen that most amino acids of $CD38_{45-74}$ were in alignment with the lentiviral sequences. To assess significance for the alignment, the inventors generated 500 random sequences with the same amino acid composition of $CD38_{45-74}$ (SEQ ID NO:1) and calculated empirically a P value as the fraction of sequences displaying an alignment with the V3 loop sequences that was as high as, or higher than that displayed by $CD38_{45-74}$. In this manner, the inventors estimate that there is a P<0.01 for an alignment as high, or higher.

As illustrated in FIG. 1B, amino acids 51-56 of human CD38 are aligned with the tips of the V3 loops of the different lentiviral envelope glycoproteins.

The accession number for the CD38 amino acid sequence (SEQ ID NO:23) in the NCBI database is: A43521. The alignments reported herein were conducted using the consensus lentiviral sequences, as they appear in the Los Alamos HIV database located on their web site. Sequence comparisons were performed using protein alignment programs.

The membrane-proximal region of the extracellular domain of CD4 can be involved in interaction with CD4. As the tip of the V3 loop was reported to bind CD4, the present inventors tested whether the GPGTTK (SEQ ID NO: 18) sequence (in frame with the tip of the V3 loop as shown in FIG. 1B) is involved in the lateral association between CD38 and CD4. CD38 cDNA lacking nucleotides encoding the GPGTTK peptide ($CD38_{\Delta52-57}$) was transfected into MT-2 cells and a transfectant (MT-2. $CD38_{\Delta52-57}$) expressing levels similar to those expressed by MT-2.CD38 cells was selected. The $CD38_{\Delta52-57}$ molecule maintained conformation-dependent characteristics such as reactivity with the IB4 antibody and GDP-ribosyl cyclase activity (not shown), thus suggesting that the tertiary structure of the molecule is not altered by the deletion.

As illustrated in FIGS. 2A, 2B and 2C, using fluorescence resonance energy transfer (FRET), a CD38 molecule lacking amino acids 51-74 corresponding to the GPGTTK (SEQ ID NO:18) hexamer ($CD38_{\Delta52-57}$) lost the lateral association with CD4 displayed by full-length CD38 (FIGS. 2A-2C). This finding is in line with results showing that CD38-derived peptides containing GPGTTK directly bind CD4 counteracting gp120/CD4 binding (see EXAMPLE III).

The present inventors also found that the membrane-proximal region of CD38 (SEQ ID NO:23) may be involved in inhibition of HIV-1 replication, as shown by the fact that $CD38_{\Delta52-57}$ lost the anti-HIV-1 inhibitory effects associated with the native CD38 molecule (FIG. 2D). This finding is in line with results using CD38-derived peptides containing GPGTTK (SEQ ID NO:18), which are endowed with inhibitory effects towards the AIDS viruses, as shown in EXAMPLE II.

The membrane-proximal region in the extracellular portion of CD38 shares significant sequence similarities with the gp120 V3 loop, which seems to correlate with effects on HIV infection: 1) both structures modulate HIV-1 fusion 2) peptides from both the V3 loop and the V3-like sequence of CD38 can bind CD4 and inhibit HIV-1 fusion (EXAMPLE I); and 3) mutations or deletions at the tip hexamer of the V3 loop and at the GPGTTK sequence of CD38 abolish the effects of these molecules on HIV-1 fusion (Example II). The hexamer at the V3 loop tip and the GPGTTK (SEQ ID NO:18) sequence of CD38 (SEQ ID NO:23) correspond to each other in the CD38/V3 loop sequence alignments (FIG. 1B).

While the present invention is not limited to any particular mechanism of action, the inventors have developed a model for CD38/CD4/gp120 interactions. The best-known function of the V3 loop is involvement in binding to chemokine receptors (CCRs). However, CD38 and CD38-derived peptides inhibited gp120 binding to human CD4 expressed in mouse cells or adsorbed on microtiter plates, in the absence of human CCRs.

The V3 loop also establishes interactions with cell surface anionic saccharidic moieties including those of glycosphingolipids (GSL), which have also been shown to bind CD38. GSL are concentrated in membrane microdomains called rafts, that contain several important signaling molecules, including CD4 and CD38. However, competition between CD38 and the V3 loop for GSL binding would explain the CD38-mediated inhibitory effects on HIV replication, but not the ability of CD38-derived peptides to down-modulate gp120/CD4 binding in the acellular model.

Another possible function of the V3 loop is to establish a secondary interaction with CD4 following the initial gp120/CD4 binding, since peptides derived from this loop bind to CD4 and some bind to a CD4 site adjacent to, but distinct from, the primary gp120-binding site in the D1 domain of CD4. Interaction of the V3 loop with CD4 does not exclude a contemporary interaction with CCR, as has been suggested for the whole gp120, whose primary binding site for CCR (i.e., the bridging sheet) also binds CD4 and is stabilized by this contact. Therefore, CD38 may compete, through its GPGTTK sequence (See SEQ ID NO:18), with this secondary interaction. The distance between the membrane-distal D1 domain of CD4, believed to interact with the V3 loop, and the membrane-proximal portion of CD38 is a weak feature of this model. The observed activity, despite the large distance, may be explained by two factors: 1) CD4 seems to be oriented obliquely to the cell surface, and 2) the D2-D3 junction confers conformational flexibility on CD4, which seems to fold following gp120 binding and allows gp120 to come close to CCRs. This folding may thus favor the interaction of CD4 with CD38 in keeping with our finding that gp120 potentiates the lateral association of CD4 with CD38. Preliminary data indicate that CD38-derived peptides bind to CD4 and inhibit binding to CD4 of a V3-loop-derived peptide. The foregoing model for the CD38/CD4/gp120 interactions is summarized in FIGS. 3 and 6.

In the EXAMPLES below, it is shown that CD38-derived peptides containing GPGTTK (SEQ ID NO: 18) abolished the binding of a V3 loop-derived peptide to CD4 and down-modulated gp120 attachment to CD4.

An alternative or complementary hypothesis is that CD38 (SEQ ID NO:23) and related peptides do not compete with portions of gp120 directly involved in CD4 binding, but destabilize the gp 120/CD4 complex by altering its energetics or electrical charge. An alteration in energetics or electronics may cause the conformational changes following initial gp 120/CD4 binding. The CD38 portion involved in the anti-HIV effects is cationic and thus may be repulsive to the highly cationic surface of gp120. Interference of CD38 with the V3 loop may also play a role in this model, since the tip of this loop is cationic and may contribute to the gp120/CD4 affinity, together with the V1 and V2 loops.

The present invention provides peptides which are useful for inhibition of transmission and inhibition of replication of the HIV virus. The peptides are derived from the CD-38 leukocyte surface antigen (SEQ ID NO:23) and include the GPGTTK sequence (SEQ ID NO:18). Peptides containing the GPGTTK sequence inhibit or prevent attachment of the HIV virus to cells. The peptides of the present invention may be combined with a pharmaceutically acceptable carrier to produce a topical cream or ointment which may be used to inhibit or prevent transmission of the HIV virus.

Alternatively, for in vivo use, the peptides of the present invention may be modified by, for example, addition of an aminoacidic, petidic or non-amino acid/non-peptidic moieties at the N— and COOH— termini of the peptides in a manner known to those skilled in the art. The peptides may also be included within the body of a protein for in vivo administration. The peptide modifications are performed in a manner which will increase the efficacy and/or stability of the peptides may be combined with a pharmaceutically acceptable carrier for in vivo administration. The modified peptide may be administered orally, either in a liquid, tablet or powder, by intradermal or intravenous injection or by any method known to those skilled in the art.

In a preferred embodiment, the peptide comprises the amino acids displayed between $CD38_{45-74}$: RWRQTWSG-PGTTKRFPETVLARCVKYTEIM (SEQ ID NO: 1). Other linear peptides which are preferred comprise the following amino acid sequences:

Peptide $CD38_{45-74}$: RWRQTWSGPGTTKRFPETV-LARCVKYTEIH (SEQ ID NO:12);

Peptide $CD38_{47-74}$: RQTWSGPGTTKRFPETV-LARCVKYTEIH (SEQ ID NO:13);

Peptide $CD38_{45-57}$: RWRQTWSGPGTTK (SEQ ID NO:14)

Peptide $CD38_{51-74}$: SGPGTTKRFPETV-LARCVKYTEIH (SEQ ID NO:15)

Peptide 7: RWRQQWSGPGTTKRFPETV-LARCVKYTEIH (SEQ ID NO: 16)

Peptide 8: RQQWSGPGTTKRFPETVLARCVKYTEIH (SEQ ID NO: 17)

In addition, branched peptides having the following configuration can inhibit or prevent the transmission or replication of HIV are also included within the scope of the present invention:

(SEQ. ID No:18)(GPGTTK)$_8$ polylysine; and (SEQ ID NO:21)(SGPGTTKRFPETVLACVKYTEIH)$_8$ polylysine.

Tests were conducted using peptide sequences set forth above to demonstrate that peptides from the 45-74 region of CD38 (SEQ ID NO:23) have antiviral effects.

The peptides set forth above were chosen for testing on the basis of the following criteria:

(a) the peptides should have only sequences present in human CD38(SEQ ID NO:23). This criterion has been applied since sequences from human molecules tend to be less immunogenic when used in humans; and (b) the peptides should contain a portion of the CD38 (SEQ ID NO:23) sequence which is significantly aligned according to at least one of the alignments shown in FIG. 1 and described above.

Preparation of Peptides

The peptides were prepared using the N alpha-9-fluorenyl-methyloxycarbonyl (Fmoc) solid phase peptide synthesis method, which involves the successive addition of amino acids to create a linear peptide chain. The C-terminus of the chain is covalently bound to a solid support, the HMP resin (4-Hydroxymethylphenoxymethyl). Amino acids are derivatized to prevent unwanted side reactions and protected at the alpha-$NH_2$ site with the Fmoc (9-fluorenylmethylcarbonyl) group (available from Perseptive Biosystem U.S.A.). During deprotection the Fmoc group is removed by piperidine in order to allow the subsequent reaction between the alfa-$NH_2$ group of the peptide-resin and the activated amino acid.

Synthesis was performed on an Automatic Peptide Synthesizer, such as, for example, the synthesizer from Applied Biosystems, mod. Synergy. The scale of synthesis is 25 micromoles, the amount of amino acid weight in each cartridge is 75 micromoles. Every amino acid is activated for 10 minutes of 0.2 M 2-(1H-benzotriazol-1-yl)1,1,3,3-tetramethyluronium hexafluorophosphate (HBTU)/hydroxybenzotriazole hidrate (HOBt) in dimethylformamide (DMF) and 0.4 M of N,N-diisopropylethylamine (DIEA) in DMF. The deprotection occurs in about 20 minutes with 20% piperidine in normal 1-methyl-2-pyrrolidone (NMP). The coupling time is 30 minutes.

The multibranched peptides are synthesized in the same manner as the linear peptides using an appropriate resin (Map). Map is a 4 or 8 branching lysine solid support and using this resin at C-terminus, the peptide chain grows on the polylysine core. Lysine has two amino groups and can be used to build up a large branching lysine complex. The epitope of interest should be at the distal flexible end of the peptide.

At the end of the synthesis the peptide-resin linkage is cleaved with a mixture of 90% trifluoroacetic acid (TFA)/ 2.5% $H_2O$/5% thioanisole/2.5% ethanedithiol or triisopropylsilane for at least 1.5 hours, with simultaneous removal of all of the side-chain protecting groups. Finally the free peptide is precipitated in methyl t-butyl-ether. The volume of ether is 10 times the volume of TFA used for the cleavage.

The isolated peptide is run on an analytical C4-C18-reversed phase high pressure liquid chromatography (HPLC) column using the conditions described in Table 2.

The invention is not limited to the foregoing method of preparing the peptides, and the peptides of the present invention may be synthesized using any method known to those skilled in the art. The linear peptides could also be obtained by biological synthesis starting from a DNA sequence encoding them. Sufficient quantities of this DNA sequence could be obtained by PCR from the CD38 cDNA (SEQ ID NO:24). Using appropriate primers, cleavage sites that can be recognized by commercially available restriction enzymes can be conferred to the amplified DNA segment. This sequence has been extensively described. The sequence of the cDNA of CD38 is also available in the NCBI database (accession number: NM 001775). The DNA segment could then be digested and ligated to appropriate vectors known to those skilled in the art and expressed in suitable organisms (bacteria, yeasts, plants). For instance, an easy method to obtain large quantities of peptides is based on their production as fusion proteins using a tag such as glutathione S-transferase (GST), from which the peptides can be easily liberated without alterations in their amino acid sequence.

The CD38-derived peptides of the present disclosure demonstrate an ability to inhibit replication of phylogenetically divergent viral isolates with no apparent cell toxicity. The inhibitory concentrations of some of these peptides are higher than those of the full-length soluble CD38 (SEQ ID NO:23), which is consistent with the view that small peptides exert a lower steric hindrance and therefore higher quantities are necessary to produce inhibition. Lower quantities of peptides can be achieved by using the longer sequences in a multiple branched form, as exemplified by $sCD38_{51-74}$ (SEQ ID NO:21) MBP, which displays inhibitory concentrations. Moreover, the present disclosure relates to the use of a human amino acid sequence to treat HIV infection, which minimizes or eliminates systemic toxicity and inflammatory phenomena in the vaginal epithelium, as often occurs with prior art topical treatments. The present disclosure also relates to use of the peptides as "topical microbicides" to limit sexual transmission of HIV.

Thus, the present inventors have shown that peptides from region 45-74 of human CD38 including the GPGTTK (SEQ ID NO: 18) motif may be used as a component of a topical treatment to prevent sexual transmission of HIV. The potential anti-HIV activity of the peptides derived from the membrane-proximal region of CD38 is shown in EXAMPLE I, EXAMPLE II and EXAMPLE IV described in detail below. Development of a safe topical "microbicide" (or prophylactic) addresses the urgent need for treatment at a time when epidemiologists are forecasting a dramatic spread of AIDS and effective vaccines are still unavailable.

In EXAMPLE V, below, the safety to cell cultures of a CD38 derived peptide is described. In particular, the lack of toxicity to HeLa cells supports the idea of using the $CD38_{51-74}$ (SEQ ID NO:21) sequence for an application in topical microbidical strategies to prevent transmission of HIV to women. Indeed, the HeLa cell line is representative of the epithelium of the uterine cervix. Part of this epithelium faces into the vaginal cavity and is the portion most delicate and exposed to damage by potentially toxic substances introduced into the vagina.

Of note, the CD38-derived peptides have no deleterious effects on viability and motility of spermatozoa, neither in normal subjects nor in those subjects with an unfavorable sperm profile. The lack of spermicidal activity should preserve the reproductive capacity of a couple, thus favoring acceptance of such a strategy by those cultures refusing contraceptive methods.

From the results reported above, a peptide having the amino acid sequence set forth in (SEQ ID NO:1) can be used to produce a topical microbiocide for use in inhibiting replication of the HIV virus. IN particular, a peptide containing the GPGTTK motif may be suitable for this purpose. The peptide may be combined with any suitable carrier known to those skilled in the art, such as gel-type lubricant. The invention is not limited in this regard, and the peptide may be included in any suitable carrier. Other ingredients typically used in topical medicaments, such as perfumes, moisturizers or other ingredients known to those skilled in the art may also be used.

Peptides 4, 5, and 6, which are water-soluble, could be used as ingredients of water-based lubricants, containing for example, cyclodextrin, sorbitol, cellulose. Some of these lubricants can per se display some anti-HIV activity, as described by Baron et al. Baron, S., "Practical prevention of Vaginal and Rectal Transmission of HIV by adapting the oral defense: use of commercial lubricants," AIDS Res Hum Retroviruses, 17: 997-1002 (2001). Therefore, it is possible to hypothesize that adding peptides 4 and 5 to these lubricants may potentiate their anti-HIV activity. A possible route of administration of the CD38-derived peptides is described in EXAMPLE IX.

General Experimental

Constructs and Transfectants

Full-length human CD38 cDNA (SEQ ID NO:24) was excised from the pCDM8 plasmid and cloned into a pcDNA3.1/zeo expression vector (Invitrogen, San Diego, Calif.) carrying ampicillin/zeocin resistance (pcDNA3.1/CD38/zeo), or pcDNA3/neo (Invitrogen) carrying ampicillin/neomycin resistance (pcDNA3/CD38/neo), as previously described in Savarino, A., Bottarel, F., Calosso, L., Feito, M. J., Bensi, T., Bragardo, M., Rojo, M. J., Pugliese, A., Abbate, I., Capobianchi, M. R., Dianzani, F., Malavasi, F. and Dianzani, U. (1999) Effects of the human CD38 glycoprotein (SEQ ID NO:23) on the early stages of the HIV-1 replication cycle. FASEB J. 13, 2265-2276, the contents of which are hereby incorporated in their entirety. Preparation of the cDNAs coding for three truncated forms lacking 15, 81, and 109 amino acids of the COOH terminal region, namely $CD38_{1-285}$, $CD38_{1-219}$, $CD38_{1-191}$, is described in Hoshino, S., Kukimoto, I., Kontani, K., Inoue, S., Kanda, Y., Malavasi, F. and Katada, T. (1997) Mapping of the catalytic and epitopic sites of human CD38/NAD+ glycohydrolase to a functional domain in the carboxyl terminus. J Immunol 158, 741-747, the contents of which are hereby incorporated in their entirety. These cDNAs were cloned into pcDNA 3.1/neo after endonuclease digestion with Hind III and Not I. A myc-tag (in italics in the sequence) was added at the NH.sub.2-terminus of the molecules by polymerase chain reaction (PCR) using primer 1 (forward) 5'-TTTAAGCTTATGGAGCAGAAGCT-GATCTCC-GAGGAGGACCTGATGGCCAACTGCG AGTTC-3' (SEQ ID NO:25) and primer 2 (reverse) 5'-TTGAATTCACCACACCATG-3' (SEQ ID NO:26). The PCR products were digested with Hind III/Eco RI (these restriction sites are in bold in the sequences) and ligated into the Hind III/EcoRI-digested plasmids coding for CD38 full-length or for the truncated forms. The cDNA coding for a CD38 molecule lacking the intracellular portion (CD $38_{24-300}$) was prepared by PCR with primer 3 (forward) 5'-AAGCTTATGCTCTGTCTTGGCGTCAG-3' (SEQ ID NO:27) and primer 2. The PCR product was digested with Hind III and Eco RI and ligated into Hind III/EcoRI-digested pcDNA3/CD38/neo.

$CD38_{\Delta52-57}$ cDNA was obtained by PCR with a CD38-specific primer (forward 5'-GGCGCCAGACGTGGAGC*CGCTTTCCCGAGACC-GTCCT-3') (SEQ ID NO:28) lacking 18 nucleotides of the CD38 sequence coding for amino acids 52-57 (GPGTTK; SEQ ID NO:18), and with primer 2. After purification, the PCR product was digested with Nar I and Eco RI and ligated into Nar I/Eco RI-digested pcDNA3/CD38/neo.

Errors in the constructs were excluded by dye-terminator cycle sequencing (Perkin Elmer, Norwalk, Conn.).

Plasmids (10 µg) linearized with PvuI were transfected into the appropriate cell line (5×10$^6$ cells in 0.8 ml of PBS) by electroporation at 960 µF and 260 mV with a Gene Pulser (Bio-Rad, Hercules, Calif.). Transfectants carrying pcDNA3/neo or pcDNA3.1/zeo were grown in media containing 0.4 mg/ml geneticin or 0.8 mg/ml zeocin respectively. The transfectants selected did not differ in growth kinetics from mock-transfected cells.

Peptides were custom-synthesized at a 95% purity rate by Primm srl., Milan, Italy, using the N-alpha-9-fluorenylmethyloxycarbonyl (Fmoc) solid phase peptide synthesis method, which involves successive addition of amino acids to create a linear peptide chain. Synthesis was performed on an Automatic Peptide Synthesizer (Applera Italia, Monza, Italy), following the manufacturer's instructions. The multi-branched peptides were synthesized in the same manner as the linear peptides using an appropriate resin (Map), i.e. an 8-branching lysine solid support (Applera Italia), originally described in Tam, J. P. (1988) Synthetic peptide vaccine design: synthesis and properties of a high-density multiple antigenic peptide system. Proc. Natl. Acad. Sci. U.S.A. 85, 5409-5413, the contents of which are hereby incorporated in their entirety. Using this resin at C-terminus, the peptide chain grew on the polylysine core. At the end of the synthesis, a mixture of 90% trifluoroacetic acid (TFA) (Advanced Biotech Italia, Seveso, Italy)+2.5% $H_2O$+5% thioanisole (Sigma-Aldrich s.r.l., Gallarate, Italy)+2.5% ethanedithiol (Sigma-Aldrich) or triisopropylsilane (Sigma-Aldrich) was used for at least 1.5 hours, for simultaneous removal of all of the side-chain protecting groups. Finally the free peptide was precipitated in methyl t-butyl-ether (Merck Eurolab, Milan, Italy). The isolated peptide was run on an analytical high pressure liquid chromatography (HPLC, Jasco Inc., Easton, Md.) using C4-C18-reversed phase columns (Phenomenex, Torrance, Calif.).

The antiviral properties of soluble CD38 (SEQ ID NO:23) and CD38-derived peptides (SEQ ID NOs:1, 12-19, 21 and 22) were tested at concentrations that did not affect cell viability.

Toxicity Assays

Cell proliferation was assessed by sequential counts of the number of live cells per ml of cell cultures by the trypan-blue exclusion method. Cell viability and apoptosis were analyzed by the methyl tetrazolium (MTT) method (Sigma-Aldrich) according to a procedure previously described in Savarino, A., Calosso, L., Piragino, A., Martini, C., Gennero, L., Pescarmona, G. P., and Pugliese, A. (1999). Modulation of surface transferrin receptors in lymphoid cells de novo infected with human immunodeficiency virus type-1. Cell. Biochem. Funct 17, 47-55, the contents of which are hereby incorporated in their entirety, and by propidium iodide/annexin V FITC staining (MedSystems Diagnostics GmbH, Vienna, Austria) following the manufacturer's instructions.

Flow Cytometry

Fluorescein isothiocyanate (FITC)-labeled mouse monoclonal antibodies (mAbs) to CD4 and CD71 were from Becton-Dickinson, San Jose, Calif.; R-phycoerythrin (R-PE)-conjugated mAbs to human CXCR-4 (12G5) were from Pharmingen, San Diego, Calif.; FITC-conjugated anti-CD38 mAbs (IB4) were obtained as previously described (32); FITC-conjugated mAbs to CD38, CD59, CD31 were from Caltag, Burlingame, Calif.; anti-CD95 FITC was from Chemicon Int., Temecula, Calif.; anti-CD4 mAbs Cy-3 were obtained as previously described in Malavasi, F., Calligaris-Cappio, F., Milanese, C., Dellabona, P., Richiardi, P., and Carbonara, A. (1984) Characterization of a murine monoclonal antibody specific for human early lymphohemopoietic cells. Hum. Immunol. 9: 9-20, the contents of which are hereby incorporated in their entirety; anti-c-myc mAbs were from Santa Cruz, Santa Cruz, Calif. Appropriate isotype-matched mAbs were used as negative controls.

Surface antigen expression was measured by standard flow cytometry techniques. Fix & Perm kit (Caltag) was used to permeabilize cells when intracellular epitopes were evaluated. Fluorescence data were collected on a 4-decade log scale and the relative fluorescence intensity was stated as the median channel number. Log values were mathematically converted to linear fluorescence intensity and the control antibody values for each experiment were subtracted to obtain median fluorescence intensity (MeFI) values.

In fluorescence resonance energy transfer (FRET) assays, cells were incubated on ice for 1 h simultaneously with Cy3-conjugated anti-CD4 mAbs (the accepting fluorophore) plus FITC-conjugated anti-CD38 mAbs (the donor fluorophore), or plus anti-CD71 FITC in negative controls. Energy transfer to Cy-3 was detected by using standard flow cytometry.

In gp120 attachment assays, cells were incubated for 30 min. at 4° C. with 2 µg/ml of FITC-conjugated HIV-1$_{IIIB}$ gp120 (gp120$_{IIIB}$, Intracell Corp, London, UK) in PBS plus 2% albumin plus 0.01% $NaN_3$ (PBS A/A) in the presence or absence of CD38 or CD38-derived molecules. Cells were then washed three times in PBS A/A, and fluorescence was acquired by flow cytometry. Fluorescence data were expressed as MeFI and normalized for CD4 expression where necessary.

Virological Assays

The laboratory-adapted HIV-1$_{IIIB}$ and HIV-1$_{P1}$ strains were used, the primary isolates HIV-1$_{UG3}$ (Clade A, R5), HIV-1$_{VI\ 829}$ (Clade C, R5), HIV-1$_{UG1}$ (Clade D, R5), HIV-1$_{CA-10}$ (CRF.sub.-01 AE, X4) (33), and HIV-2$_{CDC\ 77618}$ (Clade A, R3/R5/X4), and the pRRL.sin.hPGK.GFP reporter construct. Viral stocks were titrated biologically by the 50% endpoint dilution method, using MT-2 cells (laboratory strains) or PHA-activated peripheral blood mononuclear cells (PBMC) (primary isolates).

In acute infection assays, the appropriate cell types were incubated at 37° C. for 2 h with the viral stock suspensions at a multiplicity of infection (MOI) of approximately 0.1, unless otherwise specified. After three washes, cells were incubated in fresh culture medium for 7 days at 37° C., and cell-free supernatants at different intervals post-infection were harvested for ELISA measurement of HIV-1 p24 (NEN Life Science Prod., Boston Mass.) or HIV-2 p27 (Coulter, Hialeah, Fla.). Where necessary, soluble CD38-derived molecules were added during the step of virus adsorption onto cells.

The effects of CD38 (SEQ ID NO:23) and related molecules on viral envelope-mediated fusion were evaluated by syncytium assays based on co-incubation of MT-2 cells with chronically HIV-$_{IIIB}$-infected H$^9$$_{IIIB}$ cells in a 10:1 ratio, as previously described in Savarino, A., Gennero, L., Chen, H. C., Serrano, D., Malavasi, F., Boelaert, J. R., Sperber, K. (2001) Anti-HIV effects of chloroquine: mechanisms of inhibition and spectrum of activity. AIDS 15, 2221-2229, the contents of which are hereby incorporated in their entirety.

EXAMPLES

Example I

Effects of CD38-Derived Peptides on HIV-1 Replication

Tests were conducted to measure the effects of a synthetic soluble peptide corresponding to amino acids 51-74 of CD38 ($CD38_{51-74}$) (SEQ ID NO:15, 21) on HIV replication. Dose-finding experiments were performed in MT-4 cells infected with HIV-1 de novo in the presence of different concentrations of $CD38_{51-74}$ and in the absence of $CD38_{51-74}$. HIV-1 p24 ELISA testing on supernatants on Day 3 post-infection demonstrated that $CD38_{51-74}$ dose-dependently inhibited HIV-1$_{IIIB}$ replication with an $EC_{50}$ of 2.2 microM and an $EC_{90}$ of 182 microM (t-test for slope: P<0.01; FIG. 4A). By contrast, no inhibition was produced by an irrelevant peptide (not shown). Syncytium assays and gp120 binding experiments (t-test for slope: P<0.05; FIGS. 4B and 4C) confirmed that amino acids 51-74 from CD38 reproduce the inhibitory effects of full-length CD38 (SEQ ID NO:23) on the early stages of HIV replication.

In experiments performed using primary HIV isolates in MT-4 cells and PBMC, $CD38_{51-74}$ (SEQ ID NO:15, 21) also inhibited replication of phylogenetically-unrelated primary isolates and in primary cultures of PBMC (FIGS. 4D-4G). In these experiments, the inventors incubated cells with $CD38_{51-74}$ at a 10 µM concentration, i.e., the lowest concentration experimentally demonstrated to decrease HIV-1 IIIB replication by more than 50%. Accordingly, the inventors found inhibition rates similar to those obtained with HIV-1 IIIB at this concentration. Of note, there was a reproducible, though less persistent inhibitory effect, also when cells had been incubated with $CD38_{51-74}$ only during the step of virus adsorption onto cells.

$CD38_{51-74}$ (10 µM) (SEQ ID NO:15, 21) did not inhibit replication of an HIV-1 vector (pRRL.sin.hPGK.GFP) pseudotyped with the VSV G envelope glycoprotein (not shown), indicating that the $CD38_{51-74}$'s effect is dependent on the HIV envelope glycoproteins.

These results demonstrate a large spectrum of activity of an endogenous structural mimic of the gp120 V3 loop. The gp120 V3 loop is a hypervariable region of gp120. Therefore, the fact that the peptide of the present invention inhibits phylogenetically-unrelated HIV isolates suggests that this peptide mimics the conserved portions of the V3 loop that allow infectivity, independently of variations in the amino acid sequence.

In de novo infection assays, the laboratory-adapted HIV-1$_{IIIB}$ and HIV-1$_{P1}$ strains 3, primary isolates (HIV-1$_{UG3}$: Clade A, R5; HIV-1$_{UG1}$: Clade D, R5; HIV-1$_{CA-10}$: $CRF_{\_01AE}$, X4; and HIV-2$_{CDC\ 77618}$: Clade A, R3/R5/X4), and the pRRL.sin.hPGK.GFP reporter construct were used. Cells were incubated at 37° C. for 2 h with the viral suspensions at a multiplicity of infection (MOI) of approximately 0.1. After three washes, the cells were incubated in fresh culture medium for 7 days at 37° C. and harvested cell-free supernatants at different intervals post-infection for ELISA measurement of HIV-1 p24 (NEN, Boston, Mass.), or of HIV-2 p27 (Coulter, Hialeah, Fla.). In assays using pRRL.sin. hPGK.GFP, flow cytometrically green-fluorescent protein expression was evaluated at three days post-infection.

In syncytium assays, MT-2 cells were co-incubated with chronically HIV-1$_{IIIB}$-infected $H^9{}_{IIIB}$ cells as previously described (Savarino et al., AIDS, 2001).

In gp120 attachment assays, cells were incubated with saturating concentrations of FITC-conjugated gp120 from the HIV-1$_{IIIB}$ strain (gp120$_{IIIB}$) (Intracell Corp, London, UK) in the presence or absence of $CD38_{51-74}$, (SEQ ID NO:15, 21), and acquired fluorescence flow-cytometrically. The MeFI was used as an estimate of gp120 binding to cells.

The $CD38_{51-74}$, (SEQ ID NO:15, 21)) peptide did not carry out toxic effects at the concentrations used. Cell viability was analyzed by trypan-blue exclusion, by the MTT method and by propidium iodide/annexin V FITC staining as determined by techniques previously validated by the present inventors.

Example II

Involvement of a GPGTTK Motif in the Anti-HIV-1 Effect of $CD38_{51-74}$, (SEQ ID NO:21) on HIV-1 Replication The involvement of the GPGTTK sequence (amino acids 52-57) (SEQ ID NO: 18) in the anti-HIV effects of CD38 was investigated to determine if the anti-HIV effects of s CD $38_{51-74}$, (SEQ ID NO:15, 21) may be due to the GPGTTK hexamer (amino acids 52-57) corresponding to the V3 loop tip in the alignments performed (FIG. 1B). There were no anti-HIV effects using a peptide ($CD38_{58-74}$) wherein amino acids 51-57 (including GPGTTK) were substituted by a random sequence (TSHALSA) maintaining the same overall charge (not shown). Instead, an octameric branched peptide construct, GPGTTK MBP, dose-dependently inhibited infection of MT-4 cells in a manner similar to $CD38_{51-74}$ (SEQ ID NO:15, 21), as described above.

The effects of an octameric-branched peptide, GPGTTK (SEQ ID NO:18) MBP, on HIV replication was tested. The MT-4 cell line was infected de novo in with HIV-1$_{IIIB}$ as described in Example I above, in the presence of different concentrations of GPGTTK MBP and without GPGTTK MBP. HIV-1 p24 ELISA testing on supernatants on Day 3 post-infection demonstrated that GPGTTK MBP dose-dependently inhibited HIV-1$_{IIIB}$ replication with an $EC_{50}$ of 4.3 µM (P<0.05; FIG. 5). By contrast, no inhibition was produced by an irrelevant peptide from the COOH-terminal (membrane distal) portion of CD38 having the amino acid sequence KNIYRPDKFLQCVKNPEDSSCTSEI (SEQ ID NO:22). These effects are likely to be exerted at an early stage of HIV replication, as the cells remained in contact with GPGTTK MBP only during the step of virus adsorption onto cells.

Figure 6:
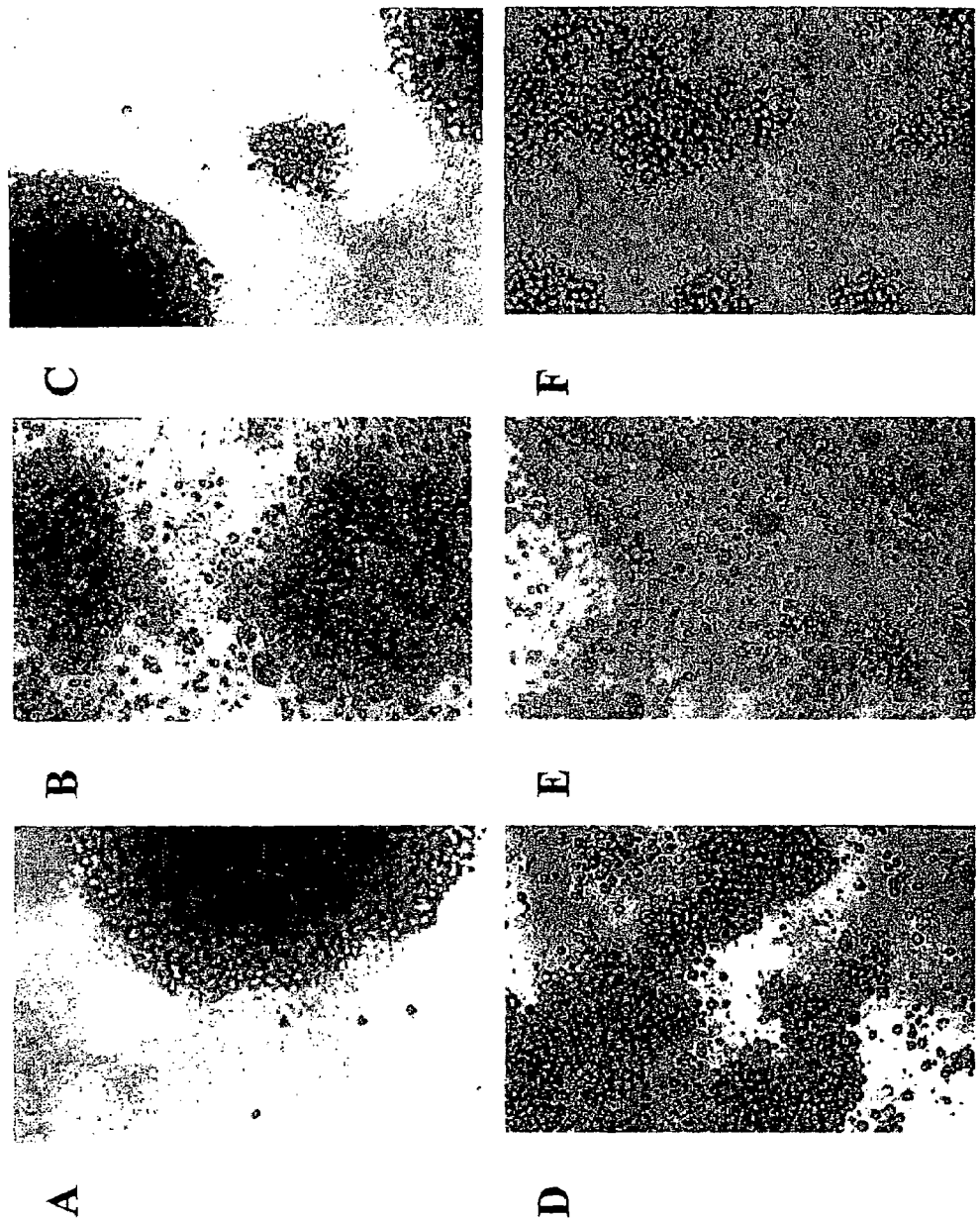

The anti-HIV effects were seen at concentrations at which no effects on cell viability were detectable. Not only had the GPGTTK-MBP peptide no toxic effects but also protected the MT-4 cells from HIV-1-related cytopathogenicity. MT-4 cells display a typical clustered pattern. When infected with HIV-1$_{IIIB}$, MT-4 cells lose the capacity of forming clusters. At five days post-infection, clusters were dissociated by pipetting, and reclustering was examined microscopically after a 3-h incubation at 37° C., as described by Pauwels et al. Pauwels, R., et al., "Sensitive and rapid assay on MT-4 cells for detection of antiviral compounds against the AIDS virus," J Virol Methods, 16: 171-185 (1987). In MT-4 cells, in fact, HIV-1$_{IIIB}$ acts as a slow/low syncytium-inducing strain whose cytopathic effect consists in loss of cell ability to cluster and is strictly correlated to the level of viral replication. When infected in the presence of GPGTTK-MBP, cultures maintained a partial ability to form clusters, whereas the untreated cultures lost this ability (FIG. 6).

Example III

The Ability of Peptides Containing GPGTTK to Bind Human CD4

Synthetic peptides from CD38 (SEQ ID NO:23) were conjugated with biotin (Pierce) as described in Wilchek, M., and Bayer, E. A., "Avidin-biotin technology," Methods Enzymol., 184:1-746 (1990). Briefly, recombinant soluble human (rsh) CD4 (2 μg/ml) (R&D Systems) was adsorbed onto wells of 96-well-ELISA plates. Wells were then saturated with phosphate buffer saline (PBS)+2% bovine serum albumin (BSA), washed with PBS+1% BSA+0.05% Triton X-100, and the plates were incubated for 2 h at 37° C. with 100 μL of different concentrations (0.1-10 μM) of biotin-conjugated peptide. After six washes, 100 microl of streptavidin-conjugated horseradish peroxidase (HRP) from a commercially available HIV-1 p24 ELISA kit (NEN) diluted 1:100 in PBS+1% BSA was added to the wells for 30 min. at room temperature. After six more washes, the wells were incubated in the dark for 30 min. at room temperature with 100 μL of o-phenylenediamine (OPD tablets-Sigma), a chromogenic substrate for HRP diluted in phosphate-citrate buffer pH 5.0 as indicated in the Manufacturer's instructions. Then, the reaction was stopped by adding to each well 100 μL of 4 N sulfuric acid. Plates were read at 450 nm using an automated ELISA reader. The optical density (O.D.) values indicate that $CD38_{51-74}$ (SEQ ID NO:15, 21) and GPGTTK-MBP associated to rshCD4 in a manner dependent on the concentration of the peptides in the incubation mixture (FIG. 7A). Negative controls were run by incubating the wells with each of the titrated peptide in the absence of rshCD4 and performing the same steps described above. The O.D. values reported in FIG. 7 were obtained by subtracting the negative control values.

The test for evaluation of rshCD4 binding was validated not only by negative controls, but also by the fact that it was capable to detect binding of recombinant gp120 from HIV-$1_{IIIB}$ when used as a positive control (FIG. 7B). Recombinant gp120 from HIV-1.sub.IIIB was conjugated with biotin and the attachment of different concentrations of this glycoprotein to rshCD4 in the presence or absence of $CD38_{51-74}$ (SEQ ID NO:15, 21) was evaluated as described above.

The inventors evaluated whether the $CD38_{51-74}$ (SEQ ID NO:15, 21) peptide might down-modulate gp120/CD4 binding. Results show that attachment of biotin-conjugated recombinant gp120 from HIV-$1_{IIIB}$ to rshCD4 was down-modulated in the presence of $CD38_{51-74}$ (SEQ ID NO:15, 21) (FIG. 7B). Indeed, the slopes of the curves obtained by plotting the gp120 concentrations against the resulting O.D. values in the presence or absence of $CD38_{51-74}$ (SEQ ID NO:15, 21) were significantly different (t-test for slope: P<0.001).

Example IV

The Effects of a Synthetic Soluble Multiple-Branched Peptide (MBP) Corresponding to Amino Acids (51-74 of CD38 ($CD38_{51-74}$ MBP) on HIV Replication Tests were conducted to measure the effects of a synthetic soluble multiple-branched peptide (MBP) corresponding to amino acids 51-74 of CD38 (SEQ ID NO:15, 21) ($CD38_{51-74}$ MBP) on HIV replication. In this construct, eight $CD38_{51-74}$ sequences are covalently bound to a polylysine core, as described above. The rationale behind these tests was that multiple-branched peptides (MBPs) are better structural mimics of short protein sequences. Dose-finding experiments were performed in MT-4 cells infected with HIV-$1_{IIIB}$ de novo in the presence of different concentrations of $CD38_{51-74}$ MBP and in the absence of $CD38_{51-74}$ MBP. HIV-1 p24 ELISA testing on supernatants on Day 3 post-infection demonstrated that $CD38_{51-74}$ dose-dependently inhibited HIV-$1_{IIIB}$ infection of the MT-4 cells in the 1-10 nanomolar range (t-test for slope: P<0.01; FIG. 8) with an $EC_{50}$ of 12 nM, an $EC_{90}$ of 75 nM, and a selectivity index of between 100 and 1000 (i.e., the ratio between the concentration capable of decreasing cell viability by 50% and the $EC_{50}$). Cell viability was assessed as described in Example V. As in these experiments $CD38_{51-74}$ MBP was added only during the step of virus adsorption onto cells, we conclude that it interferes with virus attachment/entry.

HIV-1 gp120 binding experiments confirmed that $CD38_{51-74}$ MBP inhibits at the level of gp120 attachment to target cells. In these experiments, MT-2 cells were incubated for 30 min. at 4° C. with saturating concentrations (5 μg/ml) of fluorescein isothiocyanate-labeled (FITC) HIV-$1_{IIIB}$ gp 120 (gp $120_{IIIB}$) in PBS plus 2% albumin plus 0.01% $NaN_3$ (PBS A/A) in the presence or absence of 50 nM $CD38_{51-74}$ MBP. Cells were then washed three times in PBS A/A, and fluorescence was acquired by flow cytometry. Results indicated that gp120 binding to cells was down-modulated by s $CD38_{51-74}$ MBP (FIG. 9).

The effects of $CD38_{51-74}$ MBP were then tested on infection of PBMC by primary HIV-1 isolates. Pilot experiments showed that it inhibited infection at lower concentrations than those needed in cell lines (i.e., in the 0.1-10 nM range) (FIG. 10A). FIG. 10B shows that $CD38_{51-74}$ MBP delayed the growth kinetics of two phylogenetically unrelated primary isolates (R5), belonging to subtype C (VI 829) and subtype A (UG3), in PBMC infected in the presence or absence of 1 nM $CD38_{51-74}$ MBP, which is the lowest concentration in the plateau of the dose-response curve shown in FIG. 10A.

The low inhibitory concentrations of $CD38_{51-74}$ MBP further support the specificity of the effects of the $CD38_{51-74}$ (SEQ ID NO:15, 21) sequence on HIV-1 replication. The fact that $CD38_{51-74}$ MBP inhibits HIV-1 replication at a range of concentrations approximately 1000-fold lower than that necessary to produce inhibition using $CD38_{51-74}$ [see Example I] is consistent with the view that small peptides exert a lower steric hindrance and therefore higher quantities are necessary to produce inhibition. In uninfected PBMC cultures, the peptide did not display any significant toxicity in the 0.1 nM-100 nM range, as shown by the cell growth kinetics, the trypan blue exclusion test, the MTT assay and annexin V/propidium iodide staining. (see Example V). An estimate, therefore, of the selectivity index is >1000. Moreover, the peptide did not activate unstimulated PBMC, as assessed by evaluating expression of the activation markers CD38, CD69 and HLA-DR (data not shown).

$CD38_{51-74}$ MBP displays effects with important pharmacological applications. Its extremely low inhibitory concentrations as well as its high selectivity index make it useful as a topical microbicide or a drug for systemic administration.

The potential importance of the anti-HIV effects of $CD38_{51-74}$ MBP is highlighted by a number of other considerations, as well. The development of HIV-1 resistance to antiretroviral drugs is considered to be a major factor contributing to virologic failure in patients receiving highly active antiretroviral therapy (HAART), and drug-resistant HIV-1 variants have been observed for all available nucleoside reverse trascriptase inhibitors (NRTI), non-nucleoside reverse trascriptase inhibitors (NNRTI) and protease inhibitors (PI). These issues highlight the need for new anti-HIV agents directed to other targets in the HIV life cycle.

The antiretroviral drugs in the prior art inhibit the viral reverse transcriptase and protease enzymes. The availability of a safe agent inhibiting the virus at the attachment/entry stage could be used alone, or as a component in a cocktail of drugs for high-risk individuals.

Example V

Safety and Toxicity

All peptides whose antiviral activity are shown herein have been demonstrated to be safe to cell cultures. The following example is based on experiments using $CD38_{51-74}$ (SEQ ID NO:15, 21) multiple-branched peptide (MBP) to show how safety of peptides was assayed.

Cells (from established cell lines or primary cultures) were resuspended at $2.5 \times 10^5$/ml in the presence of 0, 0.1, 1, 10 and 100 nM $CD38_{51-74}$ MBP. Then, 200 µL portions were transferred to microtiter trays and maintained at 37° C. Cells were incubated with the test compound during the whole incubation period. Cell viability was monitored daily by trypan blue-dye exclusion. Cell proliferation was assessed by sequential counts of the number of live cells per ml of cell cultures by the trypan-blue exclusion method. Cell viability and apoptosis were analyzed by the methyl tetrazolium (MTT) method, and by propidium iodide/annexin V fluorescein isothiocyanate (FITC) staining following the manufacturer's instructions.

After incubation of the cell cultures in microtiter trays as discussed in the previous paragraph, 100 µL was removed prior to the addition of 25 µL of a 5 mg/ml stock solution of MTT in PBS. After incubation for 2 h at 37° C., 100 µL extraction buffer (12.5% sodium dodecyl-sulfate, 45% dimethylformamide; pH 4.7) was added to dissolve dye-protein complexes. After overnight incubation at 37° C., the optical densities at 570 nm were measured in a automated ELISA plate reader, employing the solubilizer as blank probe.

Fluorescein isothiocyanate (FITC)-labeled Annexin V, a phospholipid-binding protein of the annexin family, was used to measure cell death using a commercially available kit (Coulter, Hialeah, Fla.). After incubating with different concentrations of CQ, the cell samples were washed in ice-cold PBS followed by centrifugation at 500×g at 4° C. The cells were stained with Annexin V FITC solution and propidium iodide and incubated for 10 minutes in the dark. The cells were analyzed by flow cytometry to measure the mean fluorescence intensity of the Annexin V positive population, gating on the live cells. Negative controls were produced by treating cells in a similar manner without adding Annexin V FITC.

Thus, at the concentrations tested, $CD38_{51-74}$ MBP does not alter cell proliferation and viability nor does it induce death of MT-4 cells, HeLa cells or primary peripheral blood mononuclear cells (PBMC, either phytohemaggltinin-stimulated or unstimulated) from three different donors.

The lack of toxicity observed on MT-4 cells and PBMC supports the specificity of the effects of $CD38_{51-74}$ MBP on HIV-1 replication. Since antiviral effects of $CD38_{51-74}$ MBP were detected at a concentration of 0.1 nM [see Example IV], and little or no toxic effects were observed using the peptide at a concentration of up to 100 nM, this combined evidence allows an estimated selectivity index of >1000.

The $CD38_{51-74}$ sequence (SEQ ID NO:15, 21) would thus be useful as a topical microbicidal agent to prevent transmission of HIV to women. The HeLa cell line is representative of the epithelium of the uterine cervix. Part of this epithelium faces into the vaginal cavity and is the portion of it most delicate and exposed to damage by potential toxic substances introduced into the vagina.

Tests were conducted to determine whether $CD38_{51-74}$ MBP might induce activation of PBMC. These experiments were devised to evaluate this because the substances proposed for use against HIV must not induce lymphocyte activation, as such activation favors HIV replication. Lymphocyte activation was assessed by evaluating expression of the activation markers CD38, CD69 and HLA-DR. For this purpose, unstimulated PBMC were incubated with 0, 0.1, 1, 10 and 100 nM $CD38_{51-74}$ MBP. The PBMC remained in contact with the peptide during the whole incubation period. At 36 h of incubation, cells were collected, washed and incubated with fluorochrome-conjugated monoclonal antibodies directed to the different activation markers. Surface antigen expression was measured by standard flow cytometry techniques. Fluorescence data were collected on a 4-decade log scale and the relative fluorescence intensity was stated as the median channel number. Log values were mathematically converted to linear fluorescence intensity and the control antibody values for each experiment were subtracted to obtain median fluorescence intensity (MeFI) values. These values indicated that $CD38_{51-74}$ MBP did not induce changes in expression of the above-mentioned lymphocyte surface markers at any of the concentrations tested, as compared to antigen expression in controls incubated in the absence of the peptide (data not shown). This test leads to the conclusion that the peptide does not activate unstimulated lymphocytes.

Also tested was cytokine release/production by non-activated primary PBMC because increases in cytokine levels in cell culture media may reflect an activation state that is not detectable by measuring surface antigen expression. After 36 h of incubation with $CD38_{51-74}$ (SEQ ID NO:15, 21) at concentrations showing antiviral activity (0.1, 1, 10 nM), none of the cytokines tested (TNF-alpha, IL-2, IL-4, IL-5, IL-6 and IL-10) was present in cell culture media at levels significantly higher than the baseline levels shown by supernatants of control untreated cells (data not shown).

Figure 18:
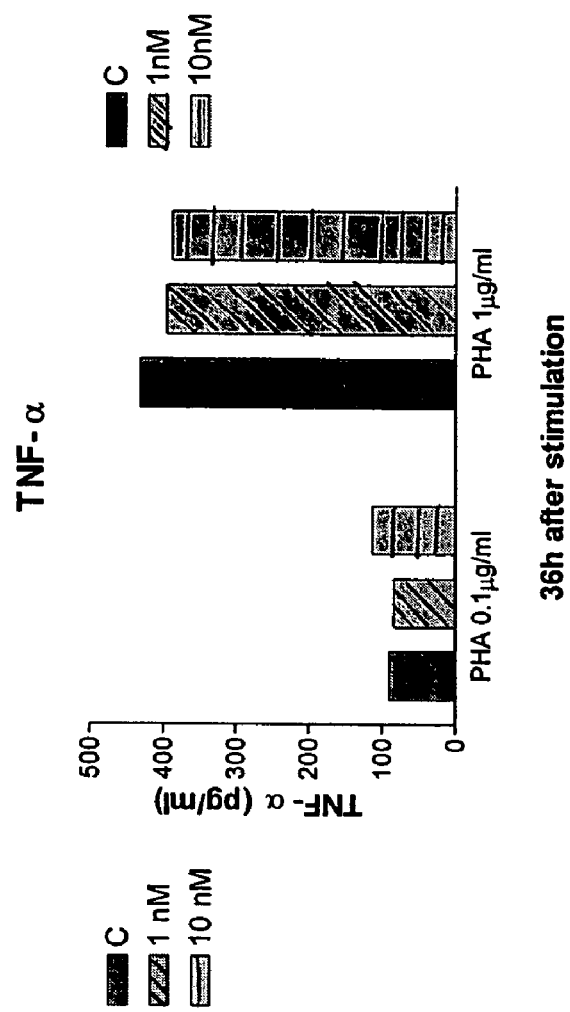

To evaluate whether $CD38_{51-74}$ MBP might costimulate activation of PBMC, tests were conducted to evaluate cytokine production in response to PHA. For this purpose, PBMC were ficoll-separated and incubated with 0, 0.1, 1, 10 nM $CD38_{51-74}$ MBP, in the presence of 0.1 or 1 µg/ml PHA. Then, supernatants were collected at 4, 12, 24, and 36 h of incubation, and the levels of TNF-alpha, IFN-gamma, IL-02, IL-4, IL-5, IL-6 and IL-10 were tested by ELISA (R and D Systems, Minneapolis, Minn.) or by cytofluorimetric multi-cytokine bead arrays (Becton-Dickinson). Results showed that IL-2, IL-4, IL-5 and IL-10 Levels were essentially identical in $CD38_{51-74}$ MBP-treated and untreated cells, independently of whether the tests were conducted with 0.1 or 1 µg/ml PHA. Some of these effects are depicted in the FIGS. 14, 15, 16 and 17. A transient and donor-dependent inhibition was observed in the case of TNF-alpha and IL-6 (FIGS. 18 and 19). This decrease did not reach statistical significance. However, if significant, it would not be of safety concern. By contrast, it would support the anti-HIV effect of $CD38_{51-74}$ MBP, since both TNF-alpha and IL-6 promote HIV-1 replication. IN particular, TNF-alpha was recently demonstrated to carry out deleterious effects in an animal model of HIV infection, its levels causing increased HIV-1 mRNA expression, acceleration of disease progression, activation of viral replication. De S K, Devadas K, Notkins A L. Elevated levels of tumor necrosis factor alpha (TNF-alpha) in human immunodeficiency virus type 1-transgenic mice: prevention of death by antibody to TNF-alpha. J Virol 2002; 76: 11710-4.

Finally, the production/release of the chemokines, macrophage inflammatory protein-1alpha (MIP-1alpha) and -1beta (MIP-1beta) was tested by ELISA (R and D Systems, Minneapolis, Minn.). These tests were conducted because, although MIP-1alpha and MIP-1beta are endowed with anti-HIV effects, an ideal topic microbicide should not induce production of these chemokines because they can attract HIV target cells to the vagina or to the rectum thus favoring rather than inhibiting infection. Results indicate that there was no induction of MIP-1alpha (not shown) and MIP-1beta (FIGS. 20 and 21 by $CD38_{51-74}$ MPB at concentrations showing antiviral activity (i.e., 1 and 10 nM) in non-stimulated and PHA-stimulated PBMC.

Example VI

Sequence Alignments

To analyze the similarities between the 45-74 sequence of CD38 ($CD38_{45-74}$) (SEQ ID NO: 1), from the NCBI RefSeq database; accession number: NP 001766) and lentiviral V3 loop sequences from the Los Alamos HIV database, binary and multiple alignments were performed using the LALIGN and DIALIGN2 software respectively. To assess the significance of the alignment, 1000 random sequences with the same amino acid composition as $CD38_{45-74}$ were generated using the RandSeq software and tested for their alignment with the V3 loop sequences. A p value was calculated empirically as the fraction of sequences displaying an alignment as high as or higher than that obtained with $CD38_{45-74}$.

The sequence similarity between CD38 (SEQ ID NO:23) and HV-1 gp120 was shown by mapping the anti-HIV activity within the 45-191 region. The membrane-proximal peptide (amino acids 45-7) shares similarities with a large portion of the V3 loop of HIV-1 gp120, including identify of the highly-conserved GPG triplet at the tip of the V3 loop (FIG. 1A). This highly conserved triplet was particularly attractive, as the tip is a partially conserved region fundamental for the regulatory effects exerted by the V3 loop on HIV-1 attachment/fusion. The generality and specificity of this similarity was examined by performing a multiple alignment between $CD38_{45-74}$ (SEQ ID NO:1) and the V3 loop consensus sequences for the principal HIV-1 group M subtypes (A, B, C, D, and $CRF_{01\_AE}$), HIV-1 groups N and O, SIV_cpz (phylogenetically close to the common ancestor of the HIV-1 groups), and HIV-2. Morgenstern's DIALIGN algorithm showed that most amino acids of $CD38_{45-74}$ were in significant alignment with the lentiviral sequences (FIG. 1B). Using 500 random sequences, its estimated that the re is a p<0.01 for an alignment as high as, or higher than that displayed between $CD38_{45-74}$ and the lentiviral V3 loops. Essentially identical results were obtained using a second published sequence for $CD38_{45-74}$ (SEQ ID NO:19) representing the membrane-proximal region of CD38 (The NCBI RefSeq accession number: D84276) (FIG. 13). This sequence presents a glutamine (Q) instead of a threonine (T) in position 49.

Example VII

CD38 Down-Modulates HIV Replication and Interferes with Envelope-Mediated Fusion This example is intended to show the specific effects of the CD38 molecule against HIV-1 fusion, thus strengthening the idea of exploiting CD38-devired peptides for therapeutic or prophylactic purposes.

In a previous study (Savarino, A., et al., "Effects of the human CD38 glycoprotein on the early stages of the HIV-1 replication cycle", The FASEB Journal, 13:2265-2276, 1999), herewith incorporated in its entirety, it was shown that CD38 (SEQ ID NO:23) inhibits HIV-1 replication at an early step of the viral life cycle, by preventing the formation of full-length proviral DNA in the human $CD4^+$ $CXCR-4^+$ MT-4 cell line and down-modulating attachment of the gp120 envelope glycoprotein to mouse T cells expressing human CD4.

The specificity of CD38 (SEQ ID NO:23) on viral envelope-mediated fusion was evaluated by using a clone of the human MT-2 T cell line (i.e., $CD4^+$ $CXCR-4^+$ $CD38^-$) stably transfected with the human full-length CD38 cDNA (SEQ ID NO:24) and expressing high levels of CD38 (MT-2.CD38 cells); a mock-transfected clone (MT-2.M cells) was used as a control. These clones were used in two types of infection assays, i.e., infection with cell-free HIV-$1_{IIIB}$ followed by evaluation of viral p24 released in the supernatant (indicator of viral replication), and co-culture with persistently HIV-1-infected $H^9_{IIIB}$ cells, followed by evaluation of syncytium formation (indicator of envelope-mediated fusion). Results showed that viral growth kinetics and syncytium formation were significantly lower in MT-2.CD38 cells than in MT-2.M cells (FIGS. 1a-c). These differences could not be ascribed to discrepancies in expression of CD4 and CXCR-4, which were similar in the two cell lines (FIG. 11A).

The effect of CD38 (SEQ ID NO:23) on gp120 attachment was evaluated by staining MT-2.M and MT-2.CD38 cells with FITC-labeled gp120$_{IIIB}$. Flow cytometry analysis showed that staining of MT-2.CD38 was weaker than that of MT-2.M cells (FIG. 11D). To test the specificity of this effect, the present inventors compared the effect of CD38 (SEQ ID NO:23) with that of other surface molecules displaying association (CD59 and CD95) or not displaying association (CD31) with CD4. No human $CD4^+$ T-cell lines lacked these molecules, so the mouse T-cell line SR.hCD4 was stably transfected with human CD4. This also allowed evaluation of CD4-mediated gp120 attachment in the absence of human HIV co-receptors. The present inventors independently transfected the cDNAs coding for the human CD59, CD95 and CD31 into SR.hCD4 cells and selected four clones expressing similar amounts of these molecules (SR.hCD4.CD38, SR.hCD4.CD59, SR.hCD4.CD95, and SR.hCD4.CD31 cells). After staining with FITC-labeled gp120$_{IIIB}$, SR.hCD4.CD38 cells were the weakest (FIG. 11D). Results showed that CD38 alone down-modulated CD4-mediated attachment of gp120 to cells and both corroborated and extended our previous observations.

Mapping of the CD38 Domain Involved in HIV-1 Inhibition

Example VIII

Identification of the CD38 Domain Involved in HIV-1 Inhibition

This example shows that the anti-HIV effects of CD38 peptides are unaffected in truncated forms that maintain the $CD38_{45-74}$ sequence (SEQ ID NO:1).

First, attention was focused on the intracellular (IC) domain of CD38. HIV-$1_{IIIB}$ was used to infect both a MT-2 cell line transfected with a truncated form of CD38 lacking the IC domain ($CD38_{24-300}$) and wild-type MT-2 cells in the presence of a recombinant soluble form of CD38 consisting solely of the extracellular (EC) domain ($sCD38_{45-300}$). Results showed that both forms inhibited HIV infection and indicate that the EC domain is sufficient for the anti-HIV activity (FIG. 12).

Next, the extracellular COOH-terminal region was evaluated by transfecting MT-2 cells with truncated forms of the CD38 cDNA (SEQ ID NO:24) coding for molecules lacking different portions of the COOH-terminal region. Since some forms lacked the epitopes recognized by the available mAbs, a myc-tag was added at the NH$_2$ terminus and their expression was assessed with an anti-myc mAb. Confocal microscopy demonstrated that all forms localized on the cell membrane (not shown), and de novo infection with HIV-1$_{IIIB}$ showed that they inhibited viral replication in a manner similar to full-length CD38 and tagCD38. (FIG. 12).

Taken together, these data show that the inhibitory activity of CD38 (SEQ ID NO:23) is located within the sequence from residues 45 to 191 unaffected by deletions of amino acids that do not involve the CD38$_{45-74}$ sequence (SEQ ID NO:1).

Example IX

Preparations Including CD38-Derived Peptides for Intravaginal or Intrarectal Use This example is intended to describe compositions containing CD38-derived peptides which may be administered to inhibit and control sexual HIV transmission. The present example is meant to serve to assist one of ordinary skill in the art in carrying out the invention and is not intended in any way to limit the scope of the invention.

In a preferred embodiment, a composition may be prepared using a dilution of 1:10 of a solution containing CD38-derived peptides (Solution A) in a non-irritating commercial lubricant such as Johnson and Johnson's Astroglide®. personal lubricant. The characteristics of this type lubricant are described in Ahmad at al.'s U.S. Pat. No. 5,885,591, the contents of which are hereby incorporated in their entirety. One important feature of this lubricant is its capability to serve as a carrier of pharmacologically active compounds to be administered to the vagina or rectum.

The resulting lubricant should contain at least one of the peptides set forth below such that the resulting lubricant contains the peptide in the following concentrations of the peptide per ml of lubricant: SEQ ID NO: 15 (4 μM-400 μM); (GPGTTK)MBP (4 μM-400 μM); CD38$_{51-74}$ MBP (4 nM to 400 nM); SEQ ID NO: 12 (4 uM-400 uM); SEQ ID NO: 13 (4 uM-400 uM); SEQ ID NO: 14 (4 uM-400 uM); SEQ ID NO: 16 (4 uM-400 uM); and SEQ ID NO: 17 (4 uM-400 uM).

The concentrations of peptides set forth in the previous paragraph are the estimated concentrations showing antiviral activity multiplied by the dilution factor in the lubricant (10×) and by the estimated dilution of the Solution A/lubricant mixture one it has come into contact with human semen (considering an intravaginal/intrarectal application of 1 ml of the Solution A/lubricant mixture and an average volume of 3 ml semen during ejaculation).

Due to their water-insolubility, peptides with sequences of SEQ ID NO: 12, SEQ ID NO: 13, SEQ ID NO: 14, SEQ ID NO: 16 and SEQ ID NO: 17 should be solubilized using cyclodextrin (at least 12K % wt/v in Solution A), wherein the cyclodextrin is selected from the group consisting of beta-cyclodextrins, derivatives of beta-cyclodextrins, alpha-cyclodextrins, derivatives of alpha-cyclodextrins, gamma-cyclodextrins, derivatives of gamma-cyclodextrins, and mixtures thereof.

As cyclodextrins per se are endowed with virucidal properties, they could be added in the same proportions to Solution A also incase it contains the water-soluble peptides 4, 5 and 6, in order to increase the anti-HIV properties of the solution.

The foregoing description is meant in an illustrative, rather than a limiting, sense, and it will be obvious to one skilled in the art that numerous changes may be made to the above-described embodiments of the present invention without departing from its spirit or scope.

What is claimed is:

1. A polypeptide useful for inhibiting the replication or transmission of the HIV virus consisting essentially of an amino acid sequence having from 13 to 30 contiguous amino acids from region 45-74 of the human CD38 leukocyte surface antigen set forth in SEQ ID NO: 1.

2. A peptide according to claim 1, consisting essentially of the amino acid sequence of SEQ ID NO: 12.

3. A peptide according to claim 1, consisting essentially of the amino acid sequence of SEQ ID NO: 13.

4. A peptide according to claim 1, consisting essentially of the amino acid sequence of SEQ ID NO: 14.

5. A peptide according to claim 1, consisting essentially of the amino acid sequence of SEQ ID NO: 15.

6. A peptide according to claim 1, consisting essentially of the amino acid sequence of SEQ ID NO. 16.

7. A peptide according to claim 1, consisting essentially of the amino acid sequence of SEQ ID NO. 17.

* * * * *